inline(12) United States Patent
Nomoto et al.

(10) Patent No.: US 7,527,963 B2
(45) Date of Patent: May 5, 2009

(54) ACETYL-COA ACYLTRANSFERASE GENE DISRUPTED BACTERIUM FOR PRODUCING POLYHYDROXYALKANOATE AND METHOD FOR PRODUCING POLYHYDROXYALKANOATE USING THE SAME

(75) Inventors: Tsuyoshi Nomoto, Tokyo (JP); Tetsuya Yano, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 323 days.

(21) Appl. No.: 11/341,504

(22) Filed: Jan. 30, 2006

(65) Prior Publication Data

US 2006/0172399 A1    Aug. 3, 2006

(30) Foreign Application Priority Data

Jan. 31, 2005    (JP) .............................. 2005-023964

(51) Int. Cl.
C12N 1/20 (2006.01)
C12N 9/10 (2006.01)
C12N 15/00 (2006.01)
C12P 1/04 (2006.01)
C12P 7/02 (2006.01)

(52) U.S. Cl. .................. 435/252.34; 435/193; 435/170; 435/155; 435/320.1

(58) Field of Classification Search ............ 435/252.34, 435/193, 170, 155, 320.1
See application file for complete search history.

(56) References Cited

U.S. PATENT DOCUMENTS

| 5,653,675 | A | 8/1997 | Kanno et al. ................. 588/249 |
| 5,665,597 | A | 9/1997 | Imamura et al. .......... 435/253.3 |
| 5,670,315 | A | 9/1997 | Yamamoto et al. .............. 435/6 |
| 5,679,568 | A | 10/1997 | Imamura et al. .......... 435/262.5 |
| 5,753,466 | A | 5/1998 | Yano et al. ................. 435/91.1 |
| 5,803,664 | A | 9/1998 | Kawabata et al. ........... 405/128 |
| 5,807,736 | A | 9/1998 | Kozaki et al. ............ 435/262.5 |
| 5,854,059 | A | 12/1998 | Kozaki et al. ............... 435/262 |
| 5,863,789 | A | 1/1999 | Komatsu et al. ............ 435/262 |
| 5,945,331 | A | 8/1999 | Kozaki et al. ............... 435/262 |
| 5,962,305 | A | 10/1999 | Mihara et al. ............ 435/262.5 |
| 6,004,772 | A | 12/1999 | Imamura et al. ............... 435/34 |
| 6,017,746 | A | 1/2000 | Imamura et al. .......... 435/252.1 |
| 6,424,418 | B2 | 7/2002 | Kawabata et al. ........... 356/445 |
| 6,472,191 | B1 | 10/2002 | Yano et al. ................... 435/189 |
| 6,479,621 | B2 | 11/2002 | Honma et al. ............... 528/361 |
| 6,586,562 | B2 | 7/2003 | Honma et al. ............... 528/361 |
| 6,649,381 | B1 | 11/2003 | Honma et al. ............... 435/135 |
| 6,660,516 | B1 | 12/2003 | Imamura et al. .......... 435/252.8 |
| 6,686,439 | B2 | 2/2004 | Kenmoku et al. ........... 528/272 |
| 6,803,444 | B2 | 10/2004 | Suzuki et al. ............... 528/361 |
| 6,808,854 | B2 | 10/2004 | Imamura et al. ............. 430/110 |
| 6,828,074 | B2 | 12/2004 | Yano et al. ............... 430/109.1 |
| 6,853,477 | B2 | 2/2005 | Nomoto et al. ............. 359/296 |
| 6,855,472 | B2 | 2/2005 | Imamura et al. .......... 430/109.4 |
| 6,858,367 | B2 | 2/2005 | Yano et al. ................... 430/109 |
| 6,858,417 | B2 | 2/2005 | Yano et al. ................... 435/189 |
| 6,861,496 | B2 | 3/2005 | Kenmoku et al. ........... 528/272 |
| 6,861,550 | B2 | 3/2005 | Honma et al. ................. 560/53 |
| 6,864,074 | B2 | 3/2005 | Yano et al. ................... 435/189 |
| 6,867,023 | B2 | 3/2005 | Honma et al. ............... 435/135 |
| 6,869,782 | B2 | 3/2005 | Kenmoku et al. ........... 435/130 |
| 6,908,720 | B2 | 6/2005 | Kenmoku et al. ............. 430/97 |
| 6,916,861 | B2 | 7/2005 | Nomoto et al. ............. 523/160 |
| 6,951,745 | B2 | 10/2005 | Nomoto et al. ............. 435/118 |
| 7,153,622 | B2 | 12/2006 | Honma et al. ............... 430/105 |
| 7,169,598 | B2 | 1/2007 | Honma et al. ............ 435/253.3 |
| 2003/0194443 | A1 | 10/2003 | Yano et al. ................... 424/497 |
| 2004/0005638 | A1 | 1/2004 | Honma et al. ................ 435/7.1 |
| 2005/0208635 | A1 | 9/2005 | Nomoto et al. ............. 435/135 |
| 2006/0172394 | A1 | 8/2006 | Kozaki et al. ............... 435/117 |
| 2006/0172398 | A1 | 8/2006 | Nomoto et al. ............. 435/135 |
| 2006/0172400 | A1 | 8/2006 | Nomoto et al. ............. 435/135 |
| 2006/0275811 | A1 | 12/2006 | Hatakeyama et al. ........... 435/6 |
| 2007/0054315 | A1 | 3/2007 | Imamura et al. .............. 435/7.1 |

OTHER PUBLICATIONS

Bhushan et al., Applied and Environmental Microbiology 69(9):5216-5221, 2003.*

Biodegradable Plastics Research Group, ed., Biodegradable Plastics Handbook, NTS Inc., 1995, pp. 178 to 197.

Hideki Abe, et al., "Biosynthesis from gluconate of a random copolyester consisting of 3-hydroxybutyrate and medium-chain-length 3-hydroxyalkanoates by *Pseudomonas* sp. 61-3", Int. J. Biol. Macromol., vol. 16, No. 3, 1994, pp. 115-119.

John Davison, et al., "Vectors with restriction site banks V. pJRD215, a wide-host-range cosmid vector with multiple cloning sites", Gene, vol. 51, Nos. 2 and 3, 1987, pp. 275-280.

Katharina Fritzsche, et al., "An unusual bacterial polyester with a phenyl pendant group", Makromol. Chem., vol. 191, 1990, pp. 1957-1965.

P. Gay, et al., "Positive Selection Procedure for Entrapment of Insertion Sequence Elements in Gram-Negative Bacteria", Journal of Bacteriology, vol. 164, No. 2, 1985, pp. 918-921.

(Continued)

*Primary Examiner*—Delia M Ramirez
(74) *Attorney, Agent, or Firm*—Fitzpatrick, Cella, Harper & Scinto

(57) ABSTRACT

A method for producing a polyhydroxyalkanoate with improved productivity and composition is provided. Polyhydroxyalkanoate is produced by a bacterium for producing polyhydroxyalkanoate in which a gene encoding acetyl-CoA acyltransferase is disrupted.

1 Claim, 3 Drawing Sheets

OTHER PUBLICATIONS

Richard A. Gross, et al., "Cyanophenoxy-Containing Microbial Polyesters: Structural Analysis, Thermal Properties, Second Harmonic Generation and In-Vivo Biodegradability", Polymer International, vol. 39, No. 3, 1996, pp. 205-213.

Y. B. Kim, et al., "Preparation and Characterization of Poly(β-hydroxyalkanoates) Obtained from *Pseudomonas oleovorans* Grown with Mixtures of 5-Phenylvaleric Acid and *n*-Alkanoic Acids", Macromolecules, vol. 24, 1991, pp. 5256-5260.

Michael E. Kovach, et al., "Four new derivatives of the broad-host-range cloning vector pBBR1MCS, carrying different antibiotic-resistance cassettes", Gene, vol. 166, 1995, pp. 175-176.

Bruce A. Ramsay, et al. "Effect of Nitrogen Limitation on Long-Side-Chain Poly-β-Hydroxyalkanoate Synthesis by *Pseudomonas resinovorans*", Applied and Environmental Microbiology, vol. 58, No. 2, Feb. 1992, pp. 744-746.

Qun Ren, et al., "FabG, an NADPH-Dependent 3-Ketoacyl Reductase of *Pseudomonas aeruginosa*, Provides Precursors for Medium-Chain-Length Poly-3-Hydroxyalkanoate Biosynthesis in *Escherichia coli*", Journal of Bacteriology, vol. 182, No. 10, May 2000, pp. 2978-2981.

R. Simon, et al., "A Broad Host Range Mobilization System for in Vivo Genetic Engineering: Transposon Mutagenesis in Gram Negative Bacteria", Bio/technology, Nov. 1983, pp. 784-791.

Henry J. Vogel, et al., "Acetylornithinase of *Escherichia coli*: Partial Purification and Some Properties", The Journal of Biological Chemistry, vol. 218, 1956, pp. 97-106.

Ohyoung Kim, et al., "Bioengineering of poly(β-hydroxyalkanoates) for advanced material applications: incorporation of cyano and nitrophenoxy side chain substituents", Canadian Journal of Microbiology, vol. 41 (Suppl. 1), 1995, pp. 32-43.

\* cited by examiner

SEQUENCE LISTING

```
<160> NUMBER OF SEQ ID NOS: 15

<210> SEQ ID NO 1
<211> LENGTH: 1176
<212> TYPE: DNA
<213> ORGANISM: Pseudomonas sp. YN21

<400> SEQUENCE: 1
atgagcttga atccaagaga cgtcgtgatt gtcgacttcg gtcgtactcc gatgggccgc      60
tccaagggcg gcatgcaccg caacacccgc gccgaagaca tgtcggcgca cctgatcagc     120
aagctgctgg aacgcaacgt caaggtcgac cctgctgaag tcgaagacgt gatctggggc     180
tgtgtgaacc agaccctgga gcagggctgg aacatcgcgc gcatggcgtc gctgatgacc     240
cagatcccgc acacctcggc cggccagacc gtcagccgcc tgtgtggctc gtcgatgagt     300
gccctgcaca cggctgcgca agcgatcatg accggcaacg gtgacgtttt cgtggttggc     360
ggcgtcgagc atatgggtca cgtgagcatg atgcacggtg tcgatccgaa cccgcacatg     420
tcgctgtacg cggcaaaagc ttcgggcatg atgggcctga ccgcggaaat gctgggcaag     480
atgcacggca tcactcgcga acagcaggac gcttttggct tgcgctccca ccaactcgcc     540
cacaaggcga ccgtggaagg caagttcaag gacgaaatca tcccgatgca gggctacgac     600
gagaacggtt tcctgaaaac cttcgactac gacgaaacca ttcgtccgga aactacccTg     660
gaaagcctgg cggctctcaa gcctgctttc aatccaaagg gtggcaccgt gaccgctggt     720
acttcgtcgc agatcaccga cggtgcctcg tgcatgatcg tgatgtcggc gcagcgtgcg     780
caggacctgg gcatccagcc tctggcggta atccgctcga tggcagtggc aggtgtggac     840
ccggcgatca tgggctatgg tccagtaccg gccacacaca aagcattgaa gcgtgcgggt     900
ctgagtatct ccgacatcga ctacttcgag ctcaacgaag ctttcgccgc acaggccttg     960
ccagtgttga aagatctgaa agtgctcgac aagatgaacg agaaggttaa cctgcacggc    1020
ggcgcgatcg ccctgggtca cccgttcggt tgctccggtg cgcggatttc cggcactttg    1080
ctgaacgtga tgaagcagaa tggcggcaac cttggggtag ccaccatgtg cattggtctc    1140
ggccaaggca tctccaccgt cttcgaacgc gtttaa                              1176

<210> SEQ ID NO 2
<211> LENGTH: 30
<212> TYPE: DNA
<213> ORGANISM: Artificial Sequence
<220> FEATURE:
<223> OTHER INFORMATION: PCR primer, fadA-f1

<400> SEQUENCE: 2
gcaccccgat gggcggatcc aagggcggca                                       30

<210> SEQ ID NO 3
<211> LENGTH: 30
```

```
<212> TYPE: DNA
<213> ORGANISM: Artificial Sequence
<220> FEATURE:
<223> OTHER INFORMATION: PCR primer, fadA-r1

<400> SEQUENCE: 3
gcgcaatcta aagcgtcct gctgttcgcg                                         30

<210> SEQ ID NO 4
<211> LENGTH: 30
<212> TYPE: DNA
<213> ORGANISM: Artificial Sequence
<220> FEATURE:
<223> OTHER INFORMATION: PCR primer, fadA-r2

<400> SEQUENCE: 4
cttgtcgagc tctttcaaat ctttcaacac                                         30

<210> SEQ ID NO 5
<211> LENGTH: 30
<212> TYPE: DNA
<213> ORGANISM: Artificial Sequence
<220> FEATURE:
<223> OTHER INFORMATION: PCR primer, pEX-f1

<400> SEQUENCE: 5
atccctagag ctcggcgtaa tcatggtcat                                         30

<210> SEQ ID NO 6
<211> LENGTH: 30
<212> TYPE: DNA
<213> ORGANISM: Artificial Sequence
<220> FEATURE:
<223> OTHER INFORMATION: PCR primer, pEX-r1

<400> SEQUENCE: 6
ttgcagcgga tccccctttc gccagctggc                                         30

<210> SEQ ID NO 7
<211> LENGTH: 6590
<212> TYPE: DNA
<213> ORGANISM: Artificial Sequence
<220> FEATURE:
<223> OTHER INFORMATION: plasmid pEX-fadA

<400> SEQUENCE: 7
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accataatcg gcattttctt ttgcgttttt atttgttaac tgttaattgt ccttgttcaa       240
ggatgctgtc tttgacaaca gatgttttct tgcctttgat gttcagcagg aagctaggcg       300
caaacgttga ttgtttgtct gcgtagaatc ctctgtttgt catatagctt gtaatcacga       360 cattgttttcc tttcgcttga ggtacagcga agtgtgagta agtaaaggtt acatcgttag       420
gatcaagatc catttttaac acaaggccag ttttgttcag cggcttgtat gggccagtta       480
aagaattaga aacataacca agcatgtaaa tatcgttaga cgtaatgccg tcaatcgtca       540
tttttgatcc gcgggagtca gtgaacagat accatttgcc gttcatttta aagacgttcg       600
cgcgttcaat ttcatctgtt actgtgttag atgcaatcag cggtttcatc acttttttca       660
gtgtgtaatc atcgtttagc tcaatcatac cgagagcgcc gtttgctaac tcagccgtgc       720
```

```
gttttttatc gctttgcaga agtttttgac tttcttgacg gaagaatgat gtgcttttgc    780
catagtatgc tttgttaaat aaagattctt cgccttggta gccatcttca gttccagtgt    840
ttgcttcaaa tactaagtat ttgtggcctt tatcttctac gtagtgagga tctctcagcg    900
tatggttgtc gcctgagctg tagttgcctt catcgatgaa ctgctgtaca ttttgatacg    960
tttttccgtc accgtcaaag attgatttat aatcctctac accgttgatg ttcaaagagc   1020
tgtctgatgc tgatacgtta acttgtgcag ttgtcagtgt ttgtttgccg taatgtttac   1080
cggagaaatc agtgtagaat aaacggattt ttccgtcaga tgtaaatgtg gctgaacctg   1140
accattcttg tgtttggtct tttaggatag aatcatttgc atcgaatttg tcgctgtctt   1200
taaagacgcg gccagcgttt ttccagctgt caatagaagt ttcgccgact ttttgataga   1260
acatgtaaat cgatgtgtca tccgcatttt taggatctcc ggctaatgca aagacgatgt   1320
ggtagccgtg atagtttgcg acagtgccgt cagcgttttg taatggccag ctgtcccaaa   1380
cgtccaggcc ttttgcagaa gagatatttt taattgtgga cgaatcgaac tcaggaactt   1440
gatattttc attttttgc tgttcaggga tttgcagcat atcatggcgt gtaatatggg   1500
aaatgccgta tgtttcctta tatggctttt ggttcgtttc tttcgcaaac gcttgagttg   1560
cgcctcctgc cagcagtgcg gtagtaaagg ttaatactgt tgcttgtttt gcaaacttt   1620
tgatgttcat cgttcatgtc tccttttta tgtactgtgt tagcggtctg cttcttccag   1680
ccctcctgtt tgaagatggc aagttagtta cgcacaataa aaaagacct aaaatatgta   1740
aggggtgacg ccaaagtata cactttgccc tttacacatt ttaggtcttg cctgctttat   1800
cagtaacaaa cccgcgcgat ttacttttcg acctcattct attagactct cgtttggatt   1860
gcaactggtc tattttcctc ttttgtttga tagaaaatca taaaaggatt tgcagactac   1920
gggcctaaag aactaaaaaa tctatctgtt tcttttcatt ctctgtattt tttatagttt   1980
ctgttgcatg gcataaagt tgccttttta atcacaattc agaaaatatc ataatatctc   2040
atttcactaa ataatagtga acggcaggta tatgtgatgg gttaaaaagg atcgatcctc   2100
tagctagagt cgatcttcgc cagcagggcg aggatcgtgg catcaccgaa ccgcgccgtg   2160
cgcgggtcgt cggtgagcca gagtttcagc aggccgccca ggcggcccag gtcgccattg   2220
atgcgggcca gctcgcggac gtgctcatag tccacgacgc ccgtgatttt gtagccctgg   2280
ccgacggcca gcaggtaggc cgacaggctc atgccggccg ccgccgcctt ttcctcaatc   2340
gctcttcgtt cgtctggaag gcagtacacc ttgataggtg ggctgccctt cctggttggc   2400
ttggtttcat cagccatccg cttgccctca tctgttacgc cggcggtagc cggccagcct   2460
cgcagagcag gattcccgtt gagcaccgcc aggtgcgaat aagggacagt gaagaaggaa   2520
cacccgctcg cgggtgggcc tacttcacct atcctgcccg gctgacgccg ttggatacac   2580
caaggaaagt ctacacgaac cctttggcaa aatcctgtat atcgtgcgaa aaaggatgga   2640
tataccgaaa aaatcgctat aatgacccg aagcagggtt atgcagcgga aaagcgctgc   2700
ttccctgctg ttttgtggaa tatctaccga ctggaaacag gcaaatgcag gaaattactg   2760
aactgagggg acaggcgaga gacgatgcca aagagctaca ccgacgagct ggccgagtgg   2820
gttgaatccc gcgcggccaa gaagcgccgg cgtgatgagg ctgcggttgc gttcctggcg   2880
gtgagggcgg atgtcgatat gcgtaaggag aaaataccgc atcaggcgca tgcatatttg   2940
aatgtattta gaaaaataaa caaaaagagt ttgtagaaac gcaaaaaggc catccgtcag   3000
gatgccttc tgcttaattt gatgcctggc agtttatggc gggcgtcctg cccgccaccc   3060
tccgggccgt tgcttcgcaa cgttcaaatc cgctcccggc ggatttgtcc tactcaggag   3120
```

```
agcgttcacc gacaaacaac agataaaacg aaaggcccag tctttcgact gagcctttcg    3180
ttttatttga tgcctggcag ttccctactc tcgcatgggg agaccccaca ctaccatcgg    3240
cgctacggcg tttcacttct gagttcggca tggggtcagg tggaccacc gcgctactgc     3300
cgccaggcaa attctgtttt atcagaccgc ttctgcgttc tgatttaatc tgtatcaggc    3360
tgaaaatctt ctctcatccg ccaaaacagc caagctcgcc attcgccatt caggctgcgc    3420
aactgttggg aagggcgatc ggtgcgggcc tcttcgctat tacgccagct ggcgaaaggg    3480
ggatccaagg gcggcaggca ccgcaccacc cgcgccgaag acatgtcggc gcacctgatc    3540
agcaagctgc tggaacgcaa cgtcaaggtc gaccctgctg aagtcgaaga cgtgatctgg    3600
ggctgtgtga accagaccct ggagcagggc tggaacatcg cgcgcatggc gtcgctgatg    3660
acccagatcc cgcacacctc ggccggccag accgtcagcc gcctgtgtgg ctcgtcgatg    3720
agtgccctgc acacggctgc gcaagcgatc atgaccggca acggtgacgt tttcgtggtt    3780
ggcggcgtcg agcatatggg tcacgtgagc atgatgcacg gtgtcgatcc gaacccgcac    3840
atgtcgctgt acgcggcaaa agcttcgggc atgatgggcc tgaccgcgga atgctgggc     3900
aagatgcacg gcatcactcg cgaacagcag gacgcttcta gattgcgctc ccaccaactc    3960
gcccacaagg cgaccgtgga aggcaagttc aaggacgaaa tcatcccgat gcagggctac    4020
gacgagaacg gtttcctgaa aaccttcgac tacgacgaaa ccattcgtcc ggaaactacc    4080
ctggaaagcc tggcggctct caagcctgct ttcaatccaa agggtggcac cgtgaccgct    4140
ggtacttcgt cgcagatcac cgacggtgcc tcgtgcatga tcgtgatgtc ggcgcagcgt    4200
gcgcaggacc tggcatcca gcctctggcg gtaatccgct cgatggcagt ggcaggtgtg     4260
gacccggcga tcatgggcta tggtccagta ccggccacac acaaagcatt gaagcgtgcg    4320
ggtctgagta tctccgacat cgactacttc gagctcggcg taatcatggt catagctgtt    4380
tcctgtgtga aattgttatc cgctcacaat tccacacaac atacgagccg gaagcataaa    4440
gtgtaaagcc tggggtgcct aatgagtgag ctaactcaca ttaattgcgt tgcgctcact    4500
gcccgctttc cagtcgggaa acctgtcgtg ccagctgcat taatgaatcg gccaacgcgc    4560
ggggagaggc ggtttgcgta ttgggcgctc ttccgcttcc tcgctcactg actcgctgcg    4620
ctcggtcgtt cggctgcggc gagcggtatc agctcactca aaggcggtaa tacgttatc     4680
cacagaatca ggggataacg caggaaagaa catgtgagca aaaggccagc aaaaggccag    4740
gaaccgtaaa aaggccgcgt tgctggcgtt tttccatagg ctccgccccc ctgacgagca    4800
tcacaaaaat cgacgctcaa gtcagaggtg gcgaaacccg acaggactat aaagatacca    4860
ggcgtttccc cctggaagct ccctcgtgcg ctctcctgtt ccgaccctgc cgcttaccgg    4920
atacctgtcc gcctttctcc cttcgggaag cgtggcgctt tctcatagct cacgctgtag    4980
gtatctcagt tcggtgtagg tcgttcgctc caagctgggc tgtgtgcacg aaccccccgt    5040
tcagcccgac cgctgcgcct tatccggtaa ctatcgtctt gagtccaacc cggtaagaca    5100
cgacttatcg ccactggcag cagccactgg taacaggatt agcagagcga ggtatgtagg    5160
cggtgctaca gagttcttga agtggtggcc taactacggc tacactagaa ggacagtatt    5220
tggtatctgc gctctgctga agccagttac cttcggaaaa agagttggta gctcttgatc    5280
cggcaaacaa accaccgctg gtagcggtgg tttttttgtt tgcaagcagc agattacgcg    5340
cagaaaaaaa ggatctcaag aagatccttt gatcttttct acgggtctg acgctcagtg     5400
gaacgaaaac tcacgttaag ggattttggt catgagatta tcaaaaagga tcttcaccta    5460
```

```
gatcctttta aattaaaaat gaagttttaa atcaatctaa agtatatatg agtaaacttg   5520
gtctgacagt taccaatgct taatcagtga ggcacctatc tcagcgatct gtctatttcg   5580
ttcatccata gttgcctgac tccccgtcgt gtagataact acgatacggg agggcttacc   5640
atctggcccc agtgctgcaa tgataccgcg agacccacgc tcaccggctc cagatttatc   5700
agcaataaac cagccagccg gaagggccga gcgcagaagt ggtcctgcaa ctttatccgc   5760
ctccatccag tctattaatt gttgccggga agctagagta agtagttcgc cagttaatag   5820
tttgcgcaac gttgttgcca ttgctacagg catcgtggtg tcacgctcgt cgtttggtat   5880
ggcttcattc agctccggtt cccaacgatc aaggcgagtt acatgatccc ccatgttgtg   5940
caaaaaagcg gttagctcct tcggtcctcc gatcgttgtc agaagtaagt tggccgcagt   6000
gttatcactc atggttatgg cagcactgca taattctctt actgtcatgc catccgtaag   6060
atgcttttct gtgactggtg agtactcaac caagtcattc tgagaatagt gtatgcggcg   6120
accgagttgc tcttgcccgg cgtcaatacg ggataatacc gcgccacata gcagaacttt   6180
aaaagtgctc atcattggaa acgttcttc ggggcgaaaa ctctcaagga tcttaccgct   6240
gttgagatcc agttcgatgt aacccactcg tgcacccaac tgatcttcag catcttttac   6300
tttcaccagc gtttctgggt gagcaaaaac aggaaggcaa aatgccgcaa aaagggaat   6360 aagggcgaca cggaaatgtt gaatactcat actcttcctt tttcaatatt attgaagcat   6420
ttatcagggt tattgtctca tgagcggata catatttgaa tgtatttaga aaaataaaca   6480
aataggggtt ccgcgcacat ttccccgaaa agtgccacct gacgtctaag aaaccattat   6540
tatcatgaca ttaacctata aaaataggcg tatcacgagg ccctttcgtc              6590

<210> SEQ ID NO 8
<211> LENGTH: 42
<212> TYPE: DNA
<213> ORGANISM: Artificial Sequence
<220> FEATURE:
<223> OTHER INFORMATION: PCR primer, gen-f1

<400> SEQUENCE: 8
attatttcta gaaggacaga aatgcctcga cttcgctgct gc                      42

<210> SEQ ID NO 9
<211> LENGTH: 45
<212> TYPE: DNA
<213> ORGANISM: Artificial Sequence
<220> FEATURE:
<223> OTHER INFORMATION: PCR primer, gen-r1

<400> SEQUENCE: 9
attatttcta gattaggtgg cggtacttgg gtcgatatca aagtg                   45

<210> SEQ ID NO 10
<211> LENGTH: 7430
<212> TYPE: DNA
<213> ORGANISM: Artificial Sequence
<220> FEATURE:
<223> OTHER INFORMATION: Acetyl-CoA acyltransferase gene-targeting
      vector pFA1

<400> SEQUENCE: 10
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
```

```
accataatcg gcatttctt ttgcgttttt atttgttaac tgttaattgt ccttgttcaa      240
ggatgctgtc tttgacaaca gatgttttct tgcctttgat gttcagcagg aagctaggcg      300
caaacgttga ttgtttgtct gcgtagaatc ctctgtttgt catatagctt gtaatcacga      360
cattgtttcc tttcgcttga ggtacagcga agtgtgagta agtaaaggtt acatcgttag      420
gatcaagatc cattttaac acaaggccag ttttgttcag cggcttgtat gggccagtta      480
aagaattaga aacataacca agcatgtaaa tatcgttaga cgtaatgccg tcaatcgtca      540
tttttgatcc gcgggagtca gtgaacagat accatttgcc gttcatttta aagacgttcg      600
cgcgttcaat ttcatctgtt actgtgttag atgcaatcag cggtttcatc acttttttca      660
gtgtgtaatc atcgtttagc tcaatcatac cgagagcgcc gtttgctaac tcagccgtgc      720
gttttttatc gctttgcaga agttttgac tttcttgacg gaagaatgat gtgcttttgc      780
catagtatgc tttgttaaat aaagattctt cgccttggta gccatcttca gttccagtgt      840
ttgcttcaaa tactaagtat ttgtggcctt tatcttctac gtagtgagga tctctcagcg      900
tatggttgtc gcctgagctg tagttgcctt catcgatgaa ctgctgtaca ttttgatacg      960
tttttccgtc accgtcaaag attgatttat aatcctctac accgttgatg ttcaaagagc     1020
tgtctgatgc tgatacgtta acttgtgcag ttgtcagtgt ttgtttgccg taatgtttac     1080
cggagaaatc agtgtagaat aaacggattt ttccgtcaga tgtaaatgtg gctgaacctg     1140
accattcttg tgtttggtct tttaggatag aatcatttgc atcgaatttg tcgctgtctt     1200
taaagacgcg gccagcgttt ttccagctgt caatagaagt ttcgccgact tttttgataga    1260 acatgtaaat cgatgtgtca tccgcatttt taggatctcc ggctaatgca aagacgatgt     1320
ggtagccgtg atagtttgcg acagtgccgt cagcgttttg taatggccag ctgtcccaaa     1380
cgtccaggcc ttttgcagaa gagatatttt taattgtgga cgaatcgaac tcaggaactt     1440 gatattttc attttttgc tgttcaggga tttgcagcat atcatggcgt gtaatatggg     1500
aaatgccgta tgtttcctta tatggctttt ggttcgtttc tttcgcaaac gcttgagttg     1560
cgcctcctgc cagcagtgcg gtagtaaagg ttaatactgt tgcttgtttt gcaaactttt     1620
tgatgttcat cgttcatgtc tcctttttta tgtactgtgt tagcggtctg cttcttccag     1680
ccctcctgtt tgaagatggc aagttagtta cgcacaataa aaaaagacct aaaatatgta     1740
aggggtgacg ccaaagtata cactttgccc tttacacatt ttaggtcttg cctgctttat     1800
cagtaacaaa cccgcgcgat ttactttcg acctcattct attagactct cgtttggatt     1860
gcaactggtc tatttcctc ttttgtttga tagaaaatca taaaaggatt tgcagactac     1920
gggcctaaag aactaaaaaa tctatctgtt tcttttcatt ctctgtattt tttatagttt     1980
ctgttgcatg ggcataaagt tgccttttta atcacaattc agaaaatatc ataatatctc     2040
atttcactaa ataatagtga acggcaggta tatgtgatgg gttaaaaagg atcgatcctc     2100
tagctagagt cgatcttcgc cagcagggcg aggatcgtgg catcaccgaa ccgcgccgtg     2160
cgcgggtcgt cggtgagcca gagtttcagc aggccgccca gcggcccag gtcgccattg      2220 atgcgggcca gctcgcggac gtgctcatag tccacgacgc ccgtgatttt gtagccctgg      2280
ccgacggcca gcaggtaggc cgacaggctc atgccggccg ccgccgcctt ttcctcaatc      2340
gctcttcgtt cgtctggaag gcagtacacc ttgataggtg ggctgccctt cctgttggc      2400 ttggtttcat cagccatccg cttgccctca tctgttacgc cggcggtagc cggccagcct      2460
cgcagagcag gattcccgtt gagcaccgcc aggtgcgaat aagggacagt gaagaaggaa      2520
cacccgctcg cgggtgggcc tacttcacct atcctgcccg gctgacgccg ttggatacac      2580
```

```
caaggaaagt ctacacgaac cctttggcaa aatcctgtat atcgtgcgaa aaaggatgga    2640
tataccgaaa aaatcgctat aatgaccccg aagcagggtt atgcagcgga aaagcgctgc    2700
ttccctgctg ttttgtggaa tatctaccga ctggaaacag gcaaatgcag gaaattactg    2760
aactgagggg acaggcgaga gacgatgcca aagagctaca ccgacgagct ggccgagtgg    2820
gttgaatccc gcgcggccaa gaagcgccgg cgtgatgagg ctgcggttgc gttcctggcg    2880
gtgagggcgg atgtcgatat gcgtaaggag aaaataccgc atcaggcgca tgcatatttg    2940
aatgtattta gaaaaataaa caaaaagagt ttgtagaaac gcaaaaaggc catccgtcag    3000
gatggccttc tgcttaattt gatgcctggc agtttatggc gggcgtcctg cccgccaccc    3060
tccgggccgt tgcttcgcaa cgttcaaatc cgctcccggc ggatttgtcc tactcaggag    3120
agcgttcacc gacaaacaac agataaaacg aaaggcccag tctttcgact gagcctttcg    3180
ttttatttga tgcctggcag ttccctactc tcgcatgggg agaccccaca ctaccatcgg    3240
cgctacggcg tttcacttct gagttcggca tggggtcagg tgggaccacc gcgctactgc    3300
cgccaggcaa attctgtttt atcagaccgc ttctgcgttc tgatttaatc tgtatcaggc    3360
tgaaaatctt ctctcatccg ccaaaacagc caagctcgcc attcgccatt caggctgcgc    3420
aactgttggg aagggcgatc ggtgcgggcc tcttcgctat tacgccagct ggcgaaaggg    3480
ggatccaagg gcggcaggca ccgcaccacc cgcgccgaag acatgtcggc gcacctgatc    3540
agcaagctgc tggaacgcaa cgtcaaggtc gaccctgctg aagtcgaaga cgtgatctgg    3600
ggctgtgtga accagaccct ggagcagggc tggaacatcg cgcgcatggc gtcgctgatg    3660
acccagatcc cgcacacctc ggccggccag accgtcagcc gcctgtgtgg ctcgtcgatg    3720
agtgccctgc acacggctgc gcaagcgatc atgaccggca acggtgacgt tttcgtggtt    3780
ggcggcgtcg agcatatggg tcacgtgagc atgatgcacg gtgtcgatcc gaacccgcac    3840
atgtcgctgt acgcggcaaa agcttcgggc atgatgggcc tgaccgcgga aatgctgggc    3900
aagatgcacg gcatcactcg cgaacagcag gacgcttcta gattaggtgg cggtacttgg    3960
gtcgatatca aagtgcatca cttcttcccg tatgcccaac tttgtataga gagccactgc    4020
gggatcgtca ccgtaatctg cttgcacgta gatcacataa gcaccaagcg cgttggcctc    4080
atgcttgagg agattgatga gcgcggtggc aatgccctgc ctccggtgct cgccggagac    4140
tgcgagatca tagatataga tctcactacg cggctgctca aacctgggca gaacgtaagc    4200
cgcgagagcg ccaacaaccg cttccttggtc gaaggcagca agcgcgatga atgtcttact    4260
acggagcaag ttcccgaggt aatcggagtc cggctgatgt tgggagtagg tggctacgtc    4320
tccgaactca cgaccgaaaa gatcaagagc agcccgcatg gatttgactt ggtcagggcc    4380
gagcctacat gtgcgaatga tgcccatact tgagccacct aactttgttt tagggcgact    4440
gccctgctgc gtaacatcgt tgctgctgcg taacatcgtt gctgctccat aacatcaaac    4500
atcgacccac ggcgtaacgc gcttgctgct tggatgcccg aggcatagac tgtacaaaaa    4560
aacagtcata acaagccatg aaaaccgcca ctgcgccgtt accaccgctg cgttcggtca    4620
aggttctgga ccagttgcgt gagcgcatac gctacttgca ttacagttta cgaaccgaac    4680
aggcttatgt caactgggtt cgtgccttca tccgtttcca cggtgtgcgt cacccggcaa    4740
ccttgggcag cagcgaagtc gaggcatttc tgtccttcta gattgcgctc ccaccaactc    4800
gcccacaagg cgaccgtgga aggcaagttc aaggacgaaa tcatcccgat gcagggctac    4860
gacgagaacg gtttcctgaa aaccttcgac tacgacgaaa ccattcgtcc ggaaactacc    4920
```

```
ctggaaagcc tggcggctct caagcctgct ttcaatccaa agggtggcac cgtgaccgct    4980
ggtacttcgt cgcagatcac cgacggtgcc tcgtgcatga tcgtgatgtc ggcgcagcgt    5040
gcgcaggacc tgggcatcca gcctctggcg gtaatccgct cgatggcagt ggcaggtgtg    5100
gacccggcga tcatgggcta tggtccagta ccggccacac acaaagcatt gaagcgtgcg    5160
ggtctgagta tctccgacat cgactacttc gagctcggcg taatcatggt catagctgtt    5220
tcctgtgtga aattgttatc cgctcacaat tccacacaac atacgagccg gaagcataaa    5280
gtgtaaagcc tggggtgcct aatgagtgag ctaactcaca ttaattgcgt tgcgctcact    5340
gcccgctttc cagtcgggaa acctgtcgtg ccagctgcat taatgaatcg gccaacgcgc    5400
ggggagaggc ggtttgcgta ttgggcgctc ttccgcttcc tcgctcactg actcgctgcg    5460
ctcggtcgtt cggctgcggc gagcggtatc agctcactca aaggcggtaa tacgttatc    5520
cacagaatca ggggataacg caggaaagaa catgtgagca aaaggccagc aaaaggccag    5580
gaaccgtaaa aaggccgcgt tgctggcgtt tttccatagg ctccgccccc ctgacgagca    5640
tcacaaaaat cgacgctcaa gtcagaggtg gcgaaacccg acaggactat aaagatacca    5700
ggcgtttccc cctggaagct ccctcgtgcg ctctcctgtt ccgaccctgc cgcttaccgg    5760
atacctgtcc gcctttctcc cttcgggaag cgtggcgctt tctcatagct cacgctgtag    5820
gtatctcagt tcggtgtagg tcgttcgctc caagctgggc tgtgtgcacg aaccccccgt    5880
tcagcccgac cgctgcgcct tatccggtaa ctatcgtctt gagtccaacc cggtaagaca    5940
cgacttatcg ccactggcag cagccactgg taacaggatt agcagagcga ggtatgtagg    6000
cggtgctaca gagttcttga agtggtggcc taactacggc tacactagaa ggacagtatt    6060
tggtatctgc gctctgctga agccagttac cttcggaaaa agagttggta gctcttgatc    6120
cggcaaacaa accaccgctg gtagcggtgg tttttttgtt tgcaagcagc agattacgcg    6180
cagaaaaaaa ggatctcaag aagatccttt gatcttttct acggggtctg acgctcagtg    6240
gaacgaaaac tcacgttaag ggattttggt catgagatta tcaaaaagga tcttcaccta    6300
gatccttta aattaaaaat gaagttttaa atcaatctaa agtatatatg agtaaacttg    6360
gtctgacagt taccaatgct taatcagtga ggcacctatc tcagcgatct gtctatttcg    6420
ttcatccata gttgcctgac tccccgtcgt gtagataact acgatacggg agggcttacc    6480
atctggcccc agtgctgcaa tgataccgcg agacccacgc tcaccggctc cagatttatc    6540
agcaataaac cagccagccg gaagggccga gcgcagaagt ggtcctgcaa ctttatccgc    6600
ctccatccag tctattaatt gttgccggga agctagagta agtagttcgc cagttaatag    6660
tttgcgcaac gttgttgcca ttgctacagg catcgtggtg tcacgctcgt cgtttggtat    6720
ggcttcattc agctccggtt cccaacgatc aaggcgagtt acatgatccc ccatgttgtg    6780
caaaaaagcg gttagctcct tcggtcctcc gatcgttgtc agaagtaagt tggccgcagt    6840
gttatcactc atggttatgg cagcactgca taattctctt actgtcatgc catccgtaag    6900
atgcttttct gtgactggtg agtactcaac caagtcattc tgagaatagt gtatgcggcg    6960
accgagttgc tcttgcccgg cgtcaatacg ggataatacc gcgccacata gcagaacttt    7020
aaaagtgctc atcattggaa acgttcttc ggggcgaaaa ctctcaagga tcttaccgct    7080
gttgagatcc agttcgatgt aacccactcg tgcacccaac tgatcttcag catcttttac    7140
tttcaccagc gtttctgggt gagcaaaaac aggaaggcaa atgccgcaa aaaagggaat    7200
aagggcgaca cggaaatgtt gaatactcat actcttcctt tttcaatatt attgaagcat    7260
ttatcagggt tattgtctca tgagcggata catatttgaa tgtatttaga aaaataaaca    7320
```

```
aatagggttt ccgcgcacat ttccccgaaa agtgccacct gacgtctaag aaaccattat        7380
tatcatgaca ttaacctata aaaataggcg tatcacgagg cccttttcgtc                  7430

<210> SEQ ID NO 11
<211> LENGTH: 1000
<212> TYPE: DNA
<213> ORGANISM: Artificial Sequence
<220> FEATURE:
<223> OTHER INFORMATION: Partial sequence for fadA gene targeting

<400> SEQUENCE: 11
gcaccgcaac acccgcgccg aagacatgtc ggcgcacctg atcagcaagc tgctggaacg          60
caacgtcaag gtcgaccctg ctgaagtcga agacgtgatc tggggctgtg tgaaccagac         120
cctggagcag ggctggaaca tcgcgcgcat ggcgtcgctg atgacccaga tcccgcacac         180
ctcggccggc cagaccgtca gccgcctgtg tggctcgtcg atgagtgccc tgcacacggc         240
tgcgcaagcg atcatgaccg gcaacggtga cgttttcgtg gttggcggcg tcgagcatat         300
gggtcacgtg agcatgatgc acggtgtcga tccgaacccg cacatgtcgc tgtacgcggc         360
aaaagcttcg ggcatgatgg gcctgaccgc ggaaatgctg ggcaagatgc acggcatcac         420
tcgcgaacag caggacgctt ttggcttgcg ctcccaccaa ctcgcccaca aggcgaccgt         480
ggaaggcaag ttcaaggacg aaatcatccc gatgcagggc tacgacgaga acggtttcct         540
gaaaaccttc gactacgacg aaaccattcg tccggaaact accctggaaa gcctggcggc         600
tctcaagcct gctttcaatc caaagggtgg caccgtgacc gctggtactt cgtcgcagat         660
caccgacggt gcctcgtgca tgatcgtgat gtcggcgcag cgtgcgcagg acctgggcat         720
ccagcctctg gcggtaatcc gctcgatggc agtggcaggt gtggaccggg cgatcatggg         780
ctatggtcca gtaccggcca cacacaaagc attgaagcgt gcgggtctga gtatctccga         840
catcgactac ttcgagctca acgaagcttt cgccgcacag gccttgccag tgttgaaaga         900
tctgaaagtg ctcgacaaga tgaacgagaa ggttaacctg cacggcggcg cgatcgccct         960
gggtcacccg ttcggttgct ccggtgcgcg gatttccggc                              1000

<210> SEQ ID NO 12
<211> LENGTH: 780
<212> TYPE: DNA
<213> ORGANISM: Artificial Sequence
<220> FEATURE:
<223> OTHER INFORMATION: Partial sequence for fadA gene targeting

<400> SEQUENCE: 12
ctgaagtcga agacgtgatc tggggctgtg tgaaccagac cctggagcag ggctggaaca          60
tcgcgcgcat ggcgtcgctg atgacccaga tcccgcacac ctcggccggc cagaccgtca         120
gccgcctgtg tggctcgtcg atgagtgccc tgcacacggc tgcgcaagcg atcatgaccg         180
gcaacggtga cgttttcgtg gttggcggcg tcgagcatat gggtcacgtg agcatgatgc         240
acggtgtcga tccgaacccg cacatgtcgc tgtacgcggc aaaagcttcg ggcatgatgg         300
gcctgaccgc ggaaatgctg ggcaagatgc acggcatcac tcgcgaacag caggacgctt         360
ttggcttgcg ctcccaccaa ctcgcccaca aggcgaccgt ggaaggcaag ttcaaggacg         420
aaatcatccc gatgcagggc tacgacgaga acggtttcct gaaaaccttc gactacgacg         480
aaaccattcg tccggaaact accctggaaa gcctggcggc tctcaagcct gctttcaatc         540
caaagggtgg caccgtgacc gctggtactt cgtcgcagat caccgacggt gcctcgtgca         600
```

| | |
|---|---|
| tgatcgtgat gtcggcgcag cgtgcgcagg acctgggcat ccagcctctg gcggtaatcc | 660 |
| gctcgatggc agtggcaggt gtggacccgg cgatcatggg ctatggtcca gtaccggcca | 720 |
| cacacaaagc attgaagcgt gcgggtctga gtatctccga catcgactac ttcgagctca | 780 |

```
<210> SEQ ID NO 13
<211> LENGTH: 552
<212> TYPE: DNA
<213> ORGANISM: Artificial Sequence
<220> FEATURE:
<223> OTHER INFORMATION: Partial sequence for fadA gene targeting

<400> SEQUENCE: 13
```

| | |
|---|---|
| gcgtcgctga tgacccagat cccgcacacc tcggccggcc agaccgtcag ccgcctgtgt | 60 |
| ggctcgtcga tgagtgccct gcacacggct gcgcaagcga tcatgaccgg caacggtgac | 120 |
| gttttcgtgg ttggcggcgt cgagcatatg ggtcacgtga gcatgatgca cggtgtcgat | 180 |
| ccgaacccgc acatgtcgct gtacgcggca aaagcttcgg gcatgatggg cctgaccgcg | 240 |
| gaaatgctgg gcaagatgca cggcatcact cgcgaacagc aggacgcttt tggcttgcgc | 300 |
| tcccaccaac tcgcccacaa ggcgaccgtg gaaggcaagt tcaaggacga aatcatcccg | 360 |
| atgcagggct acgacgagaa cggtttcctg aaaaccttcg actacgacga aaccattcgt | 420 |
| ccggaaacta ccctggaaag cctggcggct ctcaagcctg ctttcaatcc aaagggtggc | 480 |
| accgtgaccg ctggtacttc gtcgcagatc accgacggtg cctcgtgcat gatcgtgatg | 540 |
| tcggcgcagc gt | 552 |

```
<210> SEQ ID NO 14
<211> LENGTH: 502
<212> TYPE: DNA
<213> ORGANISM: Artificial Sequence
<220> FEATURE:
<223> OTHER INFORMATION: Partial sequence for fadA gene targeting

<400> SEQUENCE: 14
```

| | |
|---|---|
| tcgtccggaa actaccctgg aaagcctggc ggctctcaag cctgctttca atccaaaggg | 60 |
| tggcaccgtg accgctggta cttcgtcgca gatcaccgac ggtgcctcgt gcatgatcgt | 120 |
| gatgtcggcg cagcgtgcgc aggacctggg catccagcct ctggcggtaa tccgctcgat | 180 |
| ggcagtggca ggtgtggacc cggcgatcat gggctatggt ccagtaccgg ccacacacaa | 240 |
| agcattgaag cgtgcgggtc tgagtatctc cgacatcgac tacttcgagc tcaacgaagc | 300 |
| tttcgccgca caggccttgc agtgttgaaa agatctgaaa gtgctcgaca agatgaacga | 360 |
| gaaggttaac ctgcacggcg gcgcgatcgc cctgggtcac ccgttcggtt gctccggtgc | 420 |
| gcggatttcc ggcactttgc tgaacgtgat gaagcagaat ggcggcaacc ttggggtagc | 480 |
| caccatgtgc attggtctcg gc | 502 |

```
<210> SEQ ID NO 15
<211> LENGTH: 153
<212> TYPE: DNA
<213> ORGANISM: Artificial Sequence
<220> FEATURE:
<223> OTHER INFORMATION: Partial sequence for fadA gene targeting
```

```
<400> SEQUENCE: 15
tgtacgcggc aaaagcttcg ggcatgatgg gcctgaccgc ggaaatgctg ggcaagatgc      60
acggcatcac tcgcgaacag caggacgctt ttggcttgcg ctcccaccaa ctcgcccaca     120
aggcgaccgt ggaaggcaag ttcaaggacg aaa                                  153
```

ACETYL-COA ACYLTRANSFERASE GENE DISRUPTED BACTERIUM FOR PRODUCING POLYHYDROXYALKANOATE AND METHOD FOR PRODUCING POLYHYDROXYALKANOATE USING THE SAME

BACKGROUND OF THE INVENTION

1. Field of the Invention

The present invention relates to a bacterium for producing polyhydroxyalkanoate in which a gene encoding acetyl-CoA acyltransferase is disrupted and a method for producing a polyhydroxyalkanoate using the above-mentioned bacterium for producing polyhydroxyalkanoate. In addition, the present invention relates to a gene targeting vector for disrupting a gene encoding acetyl-CoA acyltransferase of a bacterium for producing polyhydroxyalkanoate and a process for disrupting a gene encoding acetyl-CoA acyltransferase of a bacterium for producing polyhydroxyalkanoate using the above-mentioned gene targeting vector.

2. Related Background Art

There have been reported till now that many bacteria produce and accumulate poly-3-hydroxybutyric acid (PHB) or other poly-3-hydroxyalkanoates (PHA) in bacterial cells ("Handbook of Biodegradable Plastics", ed. by Research Group on Biodegradable Plastics, NTS Co., Ltd., P178-197 (1995)). These polymers can be used for the production of various products through melt processing and the like similarly as conventional plastics. Furthermore, they have an advantage that they are completely decomposed in nature by bacteria because they are biodegradable, and they do not remain and cause pollution in natural environments like many conventional synthetic polymer compound. In addition, they are excellent in biocompatibility, and application as soft members for medical use is also expected. Particularly, considering wide application of PHA produced by microorganisms, for example, application as functional polymers, it is recently expected that "unusual PHA", PHA in which a substituent group other than alkyl group is introduced into the side chain, is extremely useful. Examples of such a substituent group include those containing an aromatic ring (phenyl group, phenoxy group, benzoyl group, etc.) and unsaturated hydrocarbons, ester group, allyl group, cyano group, halogenated hydrocarbons, epoxides and thioethers. It is known that PHA produced by microorganisms can have various compositions and structures by the type of bacteria, medium composition, culture condition, etc. to be used for the production thereof, and various researches have been conducted on the bacteria which produce such PHA and biosynthetic pathway of PHA has been comparatively well investigated. So far, three pathways have been mainly proposed as the biosynthetic pathway of PHA by microorganisms.

The "first pathway" is a pathway synthesizing poly-3-hydroxybutyric acid (PHB), in which acetyl-CoA produced through glycolysis from sugar is condensed by β-ketothiolase to give acetoacetyl-CoA which is converted to (R)-3-hydroxybutyryl-CoA by acetoacetyl-CoA reductase and then converted to PHB by polyhydroxybutyrate synthetase.

The "second pathway" is one in which (R)-3-hydroxyacyl-ACP produced through fatty acid synthesis pathway from sugar is converted to (R)-3-hydroxyacyl-CoA by (R)-3-hydroxyacyl-ACP-CoA transferase, and this serves as a substrate of polyhydroxyalkanoate synthetic enzyme, and is converted to PHA (here, ACP is the abbreviation of acyl carrier protein.).

Whereas the starting material of the first and second pathways is a sugar, the "third pathway" is one in which trans-2,3-dehydroacyl-CoA, (S)-3-hydroxyacyl-CoA or 3-ketoacyl-CoA produced through β-oxidation pathway from fatty acid is converted to (R)-3-hydroxyacyl-CoA respectively by (R)-enoyl-CoA hydratase, 3-hydroxyacyl-CoA epimerase or ketoacyl-CoA reductase, and this serve as a substrate of polyhydroxyalkanoate synthetase and is converted to PHA.

Generally, when an unusual PHA is to be produced by microorganisms, PHA producing bacteria are cultured with an alkanoate having a substituent group to be introduced added to the culture broth. Therefore, alkanoates having an unusual substituent group will be synthesized into PHA mainly through the "third pathway" using β-oxidation system. The outline of the third pathway is shown in FIG. 2.

In order to stably obtain PHA (in particular, unusual PHA) expected as a functional polymer in low cost and large quantities, it is necessary to achieve optimization as a whole of the flow of the biochemical transformation which intermediate metabolites constituting PHA synthesis/metabolic system in bacteria are subjected to so that PHA productivity may be increased. From this point of view, when an unusual PHA is produced by microorganisms, a method of using an alkanoate having a substituent group to be introduced as carbon source for replication as well as a raw material of polymer has been used for the purpose of improving the production.

Also commonly used is a method comprising extracting PHA after culturing a microorganism in a culture medium in which fatty acids of middle chain length such as octanoic acid and nonanoic acid are allowed to coexist as carbon source for replication in addition to the alkanoate having a substituent group to be introduced.

It is also shown in Journal of Bacteriology 182, 2978-2981 (2000) that intracellular PHA (usual mcl PHA) content (% cell dry weight) was able to be improved as a result of transforming fadA (acetyl-CoA acyltransferase) gene disrupted strain of "*Escherichia coli* bacterium" with PhaC2 (PHA synthetase derived from *Pseudomonas oleovolans*) and fabG (3-ketoacyl-CoA reductase derived from *Pseudomonas aeruginosa* PAO1).

(Non-patent document 1) "Handbook of Biodegradable Plastics", ed. by Research Group on Biodegradable Plastics, NTS Co., Ltd., P178-197 (1995).

(Non-patent document 2) Journal of Bacteriology 182, 2978-2981(2000)

SUMMARY OF THE INVENTION

When application of PHA to the functional polymer having biodegradability is taken into consideration, development of a biosynthesis method for obtaining "unusual PHA" in high purity is necessary, and development of a microorganism which can effectively biosynthesize such a polymer in high purity and accumulate the polymer in the cell is useful and important. It is also important to search for improvement of physical properties in a wider range in order to expand applications of PHA produced by microorganisms, and development and search of PHA containing a desired monomer unit alone, a process for producing the same, and a microorganism which can produce PHA containing a desired monomer unit alone are essential.

Because a part of monomer is used as energy source as a matter of course in the conventional method of using an alkanoate having a substituent group to be introduced as carbon source for replication as well as a raw material of polymer, there is a problem that yield of synthesized PHA decreases. In addition, there is a problem that the alkanoate which can be used as a substrate of PHA is limited because supply of energy source based on generation of acetyl-CoA by β-oxidation from the alkanoate is expected in this method and it is not possible to generate acetyl-CoA by β-oxidation in such a method unless the substrate has a chain length to some extent. Generally, substrates which have been shortened by two methylene chains by β-oxidation are newly generated and these are taken as monomer units of PHA and therefore, synthesized PHA tends to be a copolymer comprising monomer units which are different in chain length by two methylene chains. For example, when a polymer is produced in a culture medium to which 8-phenoxyoctanoic acid is added as a monomer substrate, a copolymer comprising three kinds of monomer units, i.e., 3-hydroxy-8-phenoxyoctanoic acid derived from the substrate 8-phenoxyoctanoic acid, 3-hydroxy-6-phenoxyhexanoic acid and 3-hydroxy-4-phenoxybutyric acid which are by-products derived from metabolic products is produced. In this aspect, it is extremely difficult to use this method when PHA consisting of a single monomer unit is to be obtained.

As for the conventional method of extracting PHA after having cultured a bacterium in a culture medium to which fatty acids of the middle length such as octanoic acid and nonanoic acid are allowed to coexist as carbon source for replication as well as an alkanoate having a substituent group to be introduced, there is a problem that purity of PHA is low, and 50% or more of the obtained polymer often contains the monomer unit derive from carbon source for replication (for example, 3-hydroxyoctanoic acid and 3-hydroxy nonanoic acids). These mcl-3HA units constituting units of "usual PHA" are adhesive polymers at normal temperature in a single composition and when they are present in PHA in a large amount, they remarkably lower the glass transition temperature (Tg) of the polymer. On this account, presence of mixed mcl-3HA monomer units is undesirable when hard polymer physical property at normal temperature is to be obtained. It is also known that such a heterogeneous side chain structure interferes intramolecular or inermolecular interaction derived from the side chain structure and significantly affects crystallinity or orientation. The presence of these mixed heterogeneous mcl-3HA monomer units is a big problem for achieving improvement of physical properties of the polymer and imparting the polymer with functionality in the conventional production process. A purification step for separating/removing the "unintended" monomer units such as mcl-3HA monomer units derived from of carbon source for replication may be added as means for solving this problem to acquire PHA which consisted of only monomer unit having a particular substituent group. However, such a step causes the operation to be complicated and has a problem that significant decrease in the yield cannot be avoided. A more serious problem is that when the intended monomer unit and unintended monomer unit form a copolymer, it is extremely difficult to remove only the unintended monomer unit. In particular, when the synthesis of PHA containing monomer units to which a group derived from unsaturated hydrocarbons, an ester group, an allyl group, a cyano group, a nitro group, a group derived from halogenated hydrocarbons, and epoxides is introduced as side chain structure is intended, the mcl-3HA monomer unit often forms a copolymer with unintended monomer units, and it is extremely difficult to remove the mcl-3HA monomer unit after synthesizing PHA.

Synthesis of usual mcl PHA has been improved in a system of fadA (acetyl-CoA acyltransferase) disrupted strain of *Escherichia coli* transformed with phaC2 and fabG, which has been formed to improve productivity of PHA from a viewpoint of metabolitic engeneering and disclosed in Journal of Bacteriology 182, 2978-2981 (2000), but unusual PHA cannot be synthesized because the fatty acid synthesis system (the above-mentioned second pathway) of *Escherichia coli* is used as a system for supplying monomer of PHA.

The present invention is to solve the above-mentioned problems, and an object thereof is to provide a microorganism which can produce PHA (unusual PHA) containing a monomer unit of various structure having a substituent group in the side chain useful as device materials and medical materials, particularly to provide a production process for obtaining an intended "unusual PHA" in high purity and high yield with low content of unintended monomer units.

The present inventors used phenylvaleric acid as a substrate and searched for bacteria having an ability of producing PHA containing 3-hydroxyphenylvaleric acid monomer unit. As a result, the present inventors have succeeded in separating a bacterium strain having a desired ability from the soil and named it as YN21 strain.

It has been searched in the Bergey's Manual of Systematic Bacteriology (1984), Volume 1 and Bergey's Manual of Determinative Bactoriology, ninth edition (1994) based on the mycological characteristics below and it has been found that the YN21 strain belongs to *Pseudomonas*. Therefore, this strain has been named *Pseudomonas* sp. YN21 strain.

*Pseudomonas* sp. YN21 strain, bacterium which the present inventors have separated from the soil as a bacterium producing a polyhydroxyalkanoate having an unusual substituent group has been deposited in Patent Microorganism Depository Center, National Institute of Advanced Industrial Science and Technology, (Chuoh No. 6, 1-1 Higashi, 1-chome, Tsukuba-City, Ibaragi-Prefecture, Japan).

The mycological characteristics of YN21 strain are as follows.

<Mycological Characteristics of YN21 Strain>

1) Morphological Characteristics
Size and morphology of the cell: *Bacillus*, 0.8 μm×1.5 to 2.0 μm
Cellular polymorphism: none
Mobility: available
Sporogenesis: none
Gram stainability: −
Colony configuration: orbicular, edges are smooth overall, low convexity, surface layer is smooth, lustrous and translucent)

2) Physiological Characteristics
Catalase activity: +
Oxidase activity: +
O/F test: Oxidative
Nitrate reduction: +
Indole production: −
Arginine dihydrolase: +
Esculin hydrolysis: −
Gelatine hydrolysis: −
Fluorochrome production in King-8B agar: +
Cumulation of poly-p-hydroxybutyric acid: −
Hydrolysis of Tween80: +
41° C. growth: −
Gluconic acid reduction: −
Levan production: −
Potato spoilage: −
Oversensitive reaction to tobacco irritation: −
Sucrose: −
Casein: −
Tyrosinase: +
Hydrogen sulfide: −

Pectin: −
Lecithinase: −
Litmus milk: B
Starch: −

3) Substrate Utilization Ability
glucose: +
L-arabinose: +
D-mannose: +
D-mannitol: −
Maltose: −
Gluconic acid: +
D-xylose: (+)
Raffinose: −
Salicin: −
Glycerin: +
D-cellobiose: −
D-melezitose: −
Lactose: −
Galactose: +
D-sorbitol: −
α-methyl-D-glucoside: −
D-ribose: (+)
Sucrose: −
Inositol: −
D-fructose: +
L-rhamnose: −
D-arabinose: −
Dulcitol: −
Melibiose: −
Adonitol: −
Starch: −
Erythritol: −
Trehalose: −
Betaine: +
DL-lactic acid: +
D-tartaric acid: −
L-tartaric acid: (+)
mesotartaric acid: +
n-capric acid: +
L-malic acid: (+)
Citric acid: +
D-saccharate: +
Levulinic acid: +
Mesaconic acid: −
Malonic acid: +
Succinic acid: +
Acetic acid: +
Propionic acid: +
n-butyric acid: +
Formic acid: −
Glutaric acid: +
D-quinic acid: +
Sebacic acid: +
p-hydroxybenzoic acid:+
Anthranilic acid: −
Pelargonic acid: +
Glyceric acid: +
γ-aminobutyric acid: +
L-leucine: +
L-serine: +
Histidine: +
L-isoleucine: +
L-arginine: +
β-alanine: +
L-tyrosine: +
L-valine: +
Homoserine: −
Sarcosine: +
Triacetin: +
Trigonelline: +
5-phenylvaleric acid: +
3-hydroxybutyric acid: +
L-asparagine: +

In addition, YN21 strain shows differences from *Pseudomonas cichorii* YN2 strain (FERM BP-7375) which is a conventional strain in physiological characteristics and substrate utilization ability such as nitrate reducing property, indole generation, glucose acidification, arginine dihydrolase activity and D-mannose utilization ability. Similarly, it is different from *Pseudomonas cichorii* H45 strain which is a conventional strain (FERM BP-7374) in nitrate reducing property, arginine dihydrolase activity, L-arabinose utilization ability and D-mannitol utilization ability, from *Pseudomonas jessenii* P161 strain (FERM BP-7376) in D-mannitol utilization ability, from *Pseudomonas putida* P91 strain (FERM BP-7373) in nitrate reducing property, L-arabinose utilization ability and D-mannose utilization ability, respectively.

The present inventors have performed cloning of the DNA which encodes acetyl-CoA acyltransferase gene derived from *Pseudomonas* sp. YN21 strain which the present inventors isolated as a bacterium for producing polyhydroxyalkanoate. The present inventors have also constructed a gene targeting vector for gene disruption of acetyl-CoA acyltransferase gene based on the base sequence of acetyl-CoA acyltransferase gene. With the use of the estblished gene targeting vector, an isogenic strain line, which is different in a certain gene (a gene encoding acetyl-CoA acyltransferase) and other genes are entirely the same, in which acetyl-CoA acyltransferase gene of YN21 strain is disrupted has been obtained by homologous recombination. The present invention has been completed by finding that the bacterium for producing polyhydroxyalkanoate in which acetyl-CoA acyltransferase gene is disrupted has an improved productivity of polyhydroxyalkanoate and that the produced polyhydroxyalkanoate is a homopolymer mainly composed of polymer units derived from the alkanoate which has been added in cultivation and that it has not been able to be produced conventionally.

According to the first aspect of the present invention, there is provided a bacterium for producing polyhydroxyalkanoate in which a gene encoding acetyl-CoA acyltransferase is disrupted.

According to the second aspect of the present invention, there is provided *Pseudomonas* sp. FA1 strain (FERM BP-08572) which is an isogenic strain line of a bacterium for producing polyhydroxyalkanoate *Pseudomonas* sp. YN21 strain (FERM BP-08569) and in which a gene encoding acetyl-CoA acyltransferase is disrupted.

According to the third aspect of the present invention, there if provided a method for producing a polyhydroxyalkanoate comprising culturing a bacterium for producing polyhydroxyalkanoate in which a gene encoding acetyl-CoA acyltransferase is disrupted and collecting polyhydroxyalkanoate from the culture broth.

According to the fourth aspect of the present invention, there is provided a targeting vector for an acetyl-CoA acyltransferase gene comprising (1) a DNA for homologous recombination selected from the group consisting of (a) a DNA containing the base sequence shown in SEQ ID NO: 1 or a portion thereof, and (b) a DNA hybridizing under stringent conditions with a DNA which is complementary to the DNA containing the base sequence shown in SEQ ID NO: 1, or a portion thereof,
(2) a portion for gene disruption of acetyl-CoA acyltransferase, and
(3) a vector, wherein these materials of the above (1) to (3) are operably linkedr.

According to the fifth aspect of the present invention, there is provided a host cell transformed by a gene targeting vector according to the fourth aspect of the present invention.

According to the sixth aspect of the present invention, there is provided a method for producing an isogenic strain of a bacterium for producing polyhydroxyalkanoate in which the gene coding for the acetyl-CoA acyltransferase is disrupted, wherein a homologous recombination of the acetyl-CoA acyltransferase gene on the chromosomal DNA of the bacterium for producing polyhydroxyalkanoate, the homologous recombination is caused by conjugation between the host cell according to the fifth aspect of the present invention and the bacterium for producing polyhydroxyalkanoate so that the gene coding for the acetyl-CoA acyltransferase is disrupted.

According to the seventh aspect of the present invention, there is provided a method for producing an isogenic strain of a bacterium for producing polyhydroxyalkanoate in which the gene coding for the acetyl-CoA acyltransferase is disrupted, wherein the gene coding for the acetyl-CoA acyltransferase is disrupted by homologous recombination between a DNA coding for the targeting vector according to the fourth aspect of the present invention and the acetyl-CoA acyltransferase gene on the chromosomal DNA of the bacterium for producing polyhydroxyalkanoate.

According to eighth aspect of the present invention, there is provided a targeting vector for an acetyl-CoA acyltransferase gene for a bacterium for producing polyhydroxyalkanoate, comprising
(1) a DNA selected from the group consisting of
  (a) a DNA containing the base sequence shown in SEQ ID NO: 1 or a portion thereof, and
  (b) a DNA hybridizing under stringent conditions with a DNA which is complementary to the DNA containing the base sequence shown in SEQ ID NO: 1, or a portion thereof,
(2) a foreign DNA,
(3) a replication gene incompatible with the replication gene of the bacterium for producing polyhydroxyalkanoate,
(4) a conjugative transfer origin gene, and
(5) a vector,
wherein these materials of the above items (1) to (5) are operably linked.

According to the ninth aspect of the present invention, there is provided a host cell transformed by a gene targeting vector according to the eighth aspect of the present invention.

According to the tenth aspect of the present invention, there is provided a method for producing an isogenic strain of a bacterium for producing polyhydroxyalkanoate in which the gene coding for the acetyl-CoA acyltransferase is disrupted, wherein a homologous recombination of the acetyl-CoA acyltransferase gene on the chromosomal DNA of the bacterium for producing polyhydroxyalkanoate, the homologous recombination is caused by conjugation between the host cell according to ninth aspect of the present invention and the bacterium for producing polyhydroxyalkanoate so that the gene coding for the acetyl-CoA acyltransferase is disrupted.

According to the eleventh aspect of the present invention, there is provided a method for producing an isogenic strain of a bacterium for producing polyhydroxyalkanoate in which the gene coding for the acetyl-CoA acyltransferase is disrupted, wherein the gene coding for the acetyl-CoA acyltransferase is disrupted by homologous recombination between a DNA coding for the targeting vector according to the eighth aspect of the present invention and the acetyl-CoA acyltransferase gene on the chromosomal DNA of the bacterium for producing polyhydroxyalkanoate.

According to the twelfth aspect of the present invention, there is provided a targeting vector for an acetyl-CoA acyltransferase gene for a bacterium for producing polyhydroxyalkanoate, comprising:
(1) a DNA selected from the group consisting of
  (a) a DNA containing the base sequence shown in SEQ ID NO: 1 or a portion thereof, and
  (b) a DNA hybridizing under stringent conditions with a DNA which is complementary to the DNA containing the base sequence shown in SEQ ID NO: 1, or a portion thereof,
(2) a foreign DNA inserted into another DNA defined by the above item (1),
(3) a replication gene incompatible with a replication gene of the bacterium for producing polyhydroxyalkanoate,
(4) a susceptibility gene,
(5) a conjugative transfer origin gene, and
(6) a vector,
wherein these materials of the above items (1) to (6) are operably linked. The sensitive gene is preferably a levansucrase gene. Althernatively, the exogenous DNA is preferably a gentamicin resistant gene or a kanamycin resistant gene.

According to the thirteenth aspect of the present invention, there is provided a host cell transformed by a gene targeting vector according to twelfth aspect of the present invention.

According to the fourteenth aspect of the present invention, there is provided a method for producing an isogenic strain of a bacterium for producing polyhydroxyalkanoate in which the gene coding for the acetyl-CoA acyltransferase is disrupted, wherein a homologous recombination of the acetyl-CoA acyltransferase gene on the chromosomal DNA of the bacterium for producing polyhydroxyalkanoate, the homologous recombination is caused by conjugation between the host cell according to thirteenth aspect of the present invention and the bacterium for producing polyhydroxyalkanoate so that the gene coding for the acetyl-CoA acyltransferase is disrupted.

According to the fifteenth aspect of the present invention, there is provided a method for producing an isogenic strain of a bacterium for producing polyhydroxyalkanoate in which the gene coding for the acetyl-CoA acyltransferase is disrupted, wherein the gene coding for the acetyl-CoA acyltransferase is disrupted by homologous recombination between a DNA coding for the targeting vector according to the twelfth aspect of the present invention and the acetyl-CoA acyltransferase gene on the chromosomal DNA of the bacterium for producing polyhydroxyalkanoate.

According to the sixteenth aspect of the present invention, there is a process for producing a fatty acid metabolic intermediate, the process comprising culturing a bacterium for producing polyhydroxyalkanoate in which a gene encoding acetyl-CoA acyltransferase is disrupted and collecting 3-oxoacyl-CoA, 3-hydroxyacyl-CoA or 2,3-trans-dehydroacyl-CoA from the culture broth.

Because acetyl-CoA acyltransferase is disrupted in the bacterium for producing polyhydroxyalkanoate provided by the present invention and characterized in that gene encoding acetyl-CoA acyltransferase is disrupted, functions of releasing acetyl-CoA and newly generating acyl-CoA which is a substrate having a chain length shortened by two methylene chains in the β-oxidation system of fatty acid break down. As a result, intracellular accumulation of trans-2,3-dehydroacyl-CoA, L-3-hydroxyacyl-CoA and 3-ketoacyl-CoA which are metabolic intermediates of β-oxidation system is caused. These metabolic intermediate products are converted to R-3-hydroxyacyl-CoA which is a substrate of PHA synthetase depending on the PHA synthetase system possessed by the PHA producing bacterium, for example, trans-2,3-dehydroacyl-CoA is subjected to biochemical transformation in a PHA producing bacterium expressing enoyl-CoA hydratase, L-3-hydroxyacyl-CoA is subjected to biochemical transformation in a PHA producing bacterium expressing 3-hydroxyacyl-CoA epimerase, and 3-ketoacyl-CoA is subjected to biochemical transformation in a PHA producing bacterium expressing ketoacyl-CoA reductase respectively.

Consequently, fatty acids are not used as energy source but used only for PHA synthesis, and if a substrate is added which can be used as energy source, it can be expected that the production of PHA increases. Further, because the step of newly generating substrates having a chain length shortened by two methylene chains is stopped by the break down of the function of acetyl-CoA acyltransferase, these are restrained from being taken in as a monomer unit of PHA. As a result, it can be expected that the synthesized PHA will be a homopolymer comprising monomer unit in which the methylene chains have the same chain length.

In particular, bacterium for producing polyhydroxyalkanoate *pseudomonas* sp. YN21 strain is isolated by the present inventors, and it has been found that the strain can synthesize various unusual PHA. Therefore, when the bacterium for producing polyhydroxyalkanoate *Pseudomonas* sp. FA1 strain which is an isogenic strain of YN21 strain and in which a gene encoding acetyl-CoA acyltransferase is disrupted is used, unusual PHA can be biosynthesized in a larger amount than ever before performed. In addition, the polymer composition can add a new function as a homopolymer which has not been able to be produced conventionally.

When cultured in a culture medium to which added fatty acids, FA1 strain also halts releasing acetyl-CoA and newly generating a substrate (acyl-CoA) having a chain length shortened by two methylene chains in the β-oxidation system of fatty acid because acetyl-CoA acyltransferase is disrupted. In addition, intracellular accumulation of trans-2,3-dehydroacyl-CoA, L-3-hydroxyacyl-CoA and 3-ketoacyl-CoA which are metabolic intermediates of β-oxidation system is caused. These metabolic intermediate products are used by PHA synthetase system possessed by FA1 strain, and it is converted to R-3-hydroxyacyl-CoA which is a substrate of PHA synthetase. As a result, fatty acids are not used as energy source but used only for PHA synthesis, and if a substrate is added which can be used as energy source, the production of PHA relatively increases. Further, because the step of newly generating substrates having a chain length shortened by two methylene chains is stopped by the break down of the function of acetyl-CoA acyltransferase, these are restrained from being taken in as a monomer unit of PHA. As a result, the synthesized PHA will be a homopolymer comprising monomer unit in which the methylene chains have the same chain length. Furthermore, unusual PHA can be biosynthesized in a higher productivity than ever before performed.

In addition, according to the present invention, a process of polyhydroxyalkanoate characterized in that the process comprises culturing a bacterium for producing polyhydroxyalkanoate in which a gene encoding acetyl-CoA acyltransferase is disrupted and collecting polyhydroxyalkanoate from the culture broth is provided. PHA can be produced with higher productivity by using a producing strain having a higher production ability than ever before.

Furthermore, according to the present invention, a targeting vector which is useful for disruption of acetyl-CoA acyltransferase gene as mentioned above can be is provided. According to the gene targeting vector of the present invention, for example, acetyl-CoA acyltransferase gene of *Pseudomonas* sp. YN21 strain and acetyl-CoA acyltransferase gene of bacterium for producing polyhydroxyalkanoate having acetyl-CoA acyltransferase gene having homology thereto can be disrupted effectively.

In addition, according to the process of the present invention for producing an isogenic strain line of polyhydroxyalkanoate producing bacteria in which a gene encoding acetyl-CoA acyltransferase is disrupted, the gene encoding acetyl-CoA acyltransferase can be simply and easily disrupted by homologous recombination of the acetyl-CoA acyltransferase gene in the chromosome DNA of the bacterium for producing polyhydroxyalkanoate with the gene targeting vector DNA of the present invention.

Furthermore, when the bacterium for producing polyhydroxyalkanoate provided by the present invention characterized in that the gene encoding acetyl-CoA acyltransferase is disrupted is cultured in a culture medium to which fatty acids are added, releasing of acetyl-CoA and new generation of a substrate (acyl-CoA) having a chain length shortened by two methylene chains are halted in the β-oxidation system of fatty acid because acetyl-CoA acyltransferase is disrupted, and intracellular accumulation of trans-2,3-dehydroacyl-CoA, L-3-hydroxyacyl-CoA and 3-ketoacyl-CoA which are metabolic intermediates of β-oxidation system is caused and therefore, it can be preferably used for producing these fatty acid metabolic intermediates. These fatty acid metabolic intermediates can be used as substrates of in vitro synthesis of PHA using polyhydroxyalkanoate synthetase.

DESCRIPTION OF THE PREFERRED EMBODIMENTS

Figure 1:
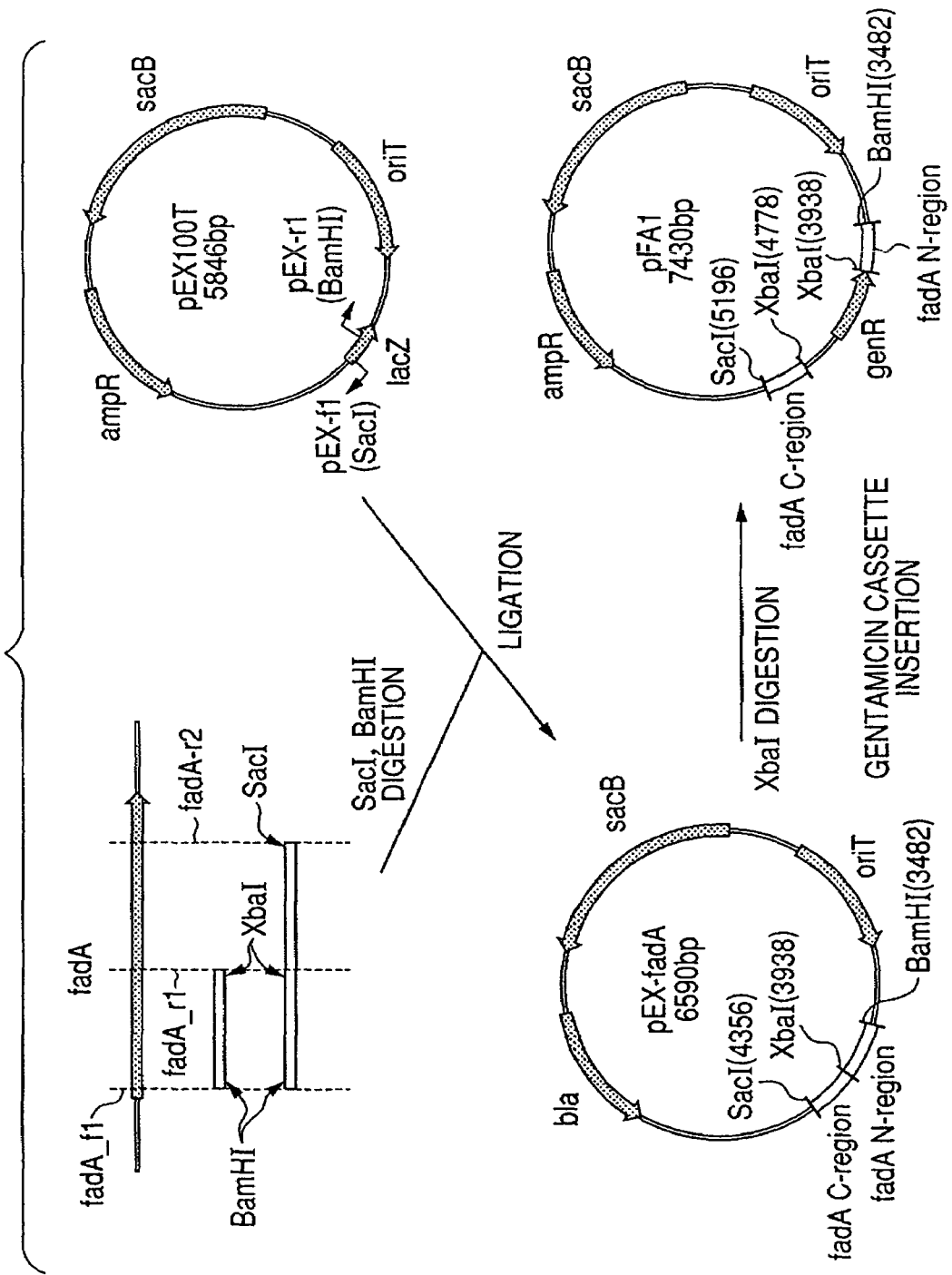
FIG. 1 illustrates the outline of procedures to construct the targeting vector for an acetyl-CoA acyltransferase gene pFA1 exemplified in Example 1.
Figure 2:
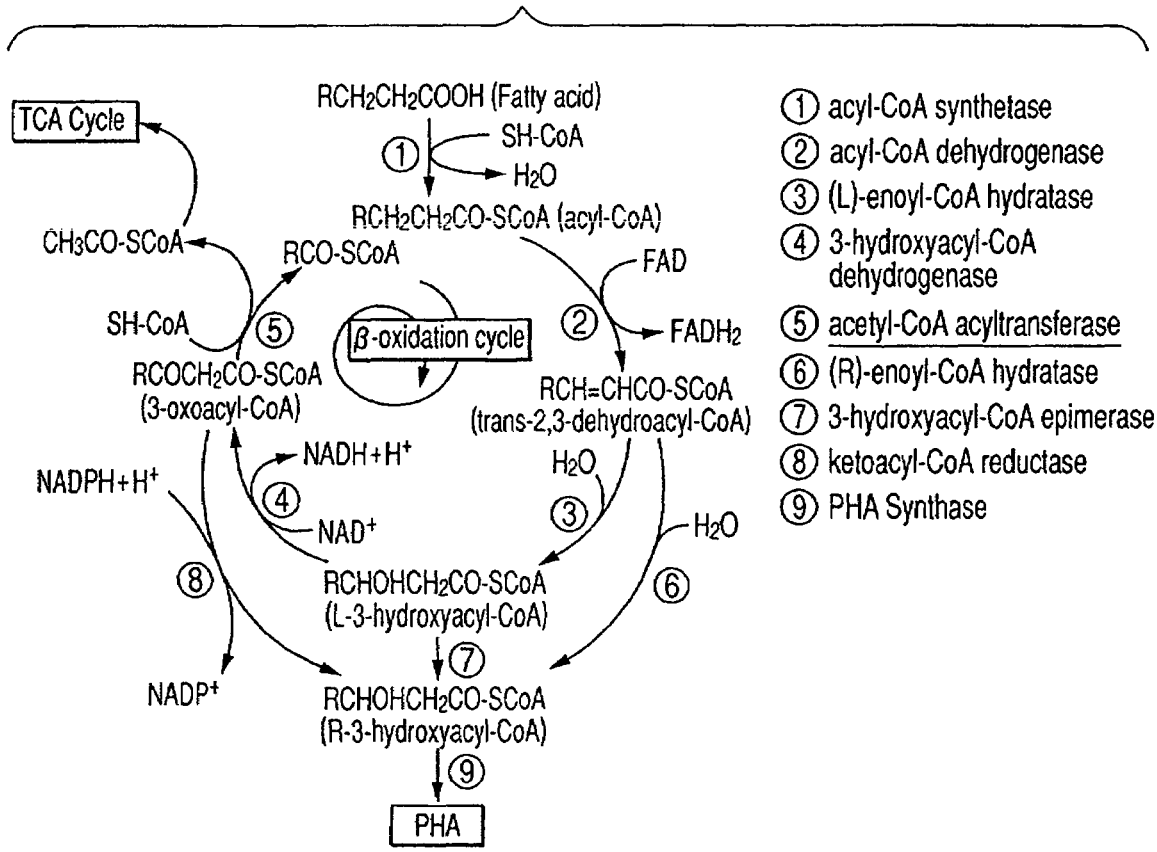
FIG. 2 illustrates the outline of the third pathway of the polyhydroxyalkanoate biosynthesis pathway by microorganism described in detail in the specification.

The polyhydroxyalkanoate (PHA) producing bacteria provided by the present invention is one among the microorganisms known to produce polyhydroxyalkanoate conventionally which possesses a functional fatty acid metabolic system and can synthesize a polyhydroxyalkanoate containing 3-hydroxyalkanoic acid derived from a fatty acid as a constituting unit and for which the produced PHA can be identified by analysis and the like procedures.

Examples of such microorganisms include *Pseudomonas oleovorans* (Makromol, Chem., 191, 1957-1965 (1990) and Macromolecules, 24, 5256-5260 (1991)), *Pseudomonas putida* (Can. J. Microbiol., 41.32-43 (1995) and Polymer International, 39, 205-213 (1996)), *Pseudomonas resino-* vorans) (Appl. Environ. Microbiol., 58 (2), 746 (1992)), Pseudomonad sp. 61-3 strains (Int. J. Biol. Macromol., 16(3), 119(1994)), Pseudomons cihorii YN2(FERM BP-7375), Pseudomonas cichorii H45 (FERM BP-7374), Pseudomonas jessenii P161 (FERM BP-7376), but are not limited to these as long as it posseses a functional fatty acid metabolic system and an ability of synthesizing a polyhydroxyalkanoate containing 3-hydroxyalkanoic acid derived from a fatty acid as a constituting unit, and polyhydroxyalkanoate producing bacteria newly found in the future can be used in the present invention.

Pseudomonas sp. YN21 strain, a bacterium which the present inventors isolated from the soil as a bacterium producing polyhydroxyalkanoate having an unusual substituent group can be preferably used in the present invention in particular.

The acetyl-CoA acyltransferase of the present invention is an enzyme catalyzing the chemical reaction:

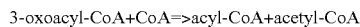

3-oxoacyl-CoA+CoA=>acyl-CoA+acetyl-CoA and represented by the enzyme number EC 2.3.1.16. The acetyl-CoA acyltransferase is commonly also known as acetyl-CoA C-acyltransferase, beta-ketothiolase, 3-ketoacyl-CoA thiolase, KAT, beta-ketoacyl-CoA thiolase, beta-ketoadipyl-CoA thiolase), 3-ketoacyl-CoA thiolase, 3-ketoacyl thiolase, 3-ketothiolase, 3-oxoacyl-CoA thiolase, 6-oxoacyl-CoA thiolase, acetoacetyl-CoA beta-ketothiolase, ketoacyl-CoA acyltransferase, ketoacyl-CoA thiolase, long-chain 3-oxoacyl-CoA thiolase, oxoacyl-CoA thiolase, pro-3-ketoacyl-CoA thiotase, thiolase I and so on. In the meantime, an enzyme which participates in PHB synthesis and catalyzes the chemical reaction (enzyme number EC 2.3.1.9):

2-acetyl-CoA=>CoA+acetoacetyl-CoA is also referred to as beta-ketothiolase, and it is commonly also known as acetyl-CoA C-acetyltransferase, acetoacetyl-CoA thiolase, beta-acetoacetyl-CoA thiolase, 2-methyl-acetoacetyl-CoA thiolase, 3-oxothiolase, acetyl-CoA thiolase, acetyl-CoA acetyltransferase, acetyl-CoA N-acetyltransferase, thiolase II but these are different from acetyl-CoA acyltransferase of the present invention. The acetyl-CoA acyltransferase of the present invention is an enzyme constituting the oxidative metabolic system of long chain length or middle chain length fatty acids, and can be distinguished whether it substantially catalyzes the chemical reaction in vivo:

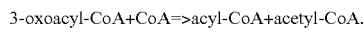

3-oxoacyl-CoA+CoA=>acyl-CoA+acetyl-CoA.

The bacterium for producing polyhydroxyalkanoate of the present invention characterized in that the gene encoding acetyl-CoA acyltransferase is disrupted can be acquired by subjecting a bacterium having a gene encoding acetyl-CoA acyltransferase and producing polyhydroxyalkanoate to mutagenic treatment leading to degeneration of the gene sequence encoding acetyl-CoA acyltransferase, integration of a transposon to gene sequence encoding acetyl-CoA acyltransferase or degeneration by genetic engineering which prevents the gene encoding the enzyme from expressing, for example, antisense gene inhibition or further selective gene disruption The chemical mutagen which is useful to raise mutation is, for example, an alkylating agent such as N-methyl-N'-nitro-N-nitrosoguanidine (NTG), ethylmethanesulfonate (EMS) and diethyl sulfate (DES). Hydroxylamine and chemicals which deaminates a DNA base such as nitrous acid are also useful. Ionizing radiation (γ- and X-ray) and ultraviolet irradiation (UV) are physical mutagens useful in mutagenesis.

Mutants in which the gene encoding acetyl-CoA acyltransferase has been disrupted can be acquired, for example, by performing the first screening utilizing the property that they cannot grow on an agar plate containing a fatty acid as single carbon source and checking the acquired clones whether the gene of acetyl-CoA acyltransferase is disrupted. Whether the gene encoding acetyl-CoA acyltransferase is disrupted can be confirmed, for example, by measuring acetyl-CoA acyltransferase activity of the bacteria fragmented liquid. Assay of acetyl-CoA acyltransferase activity can be carried out, for example, by adding the reaction mixture having a composition of Table 1 in 1.0 ml volume quartz cell and adjusting the temperature to 37° C., adding 20 μl of the bacteria fragmented liquid and reacting them at 37° C. and determining the decrease of 3-oxopalmitoyl CoA consumed by measuring the absorbance at a wavelength of 303 nm (OD303).

TABLE 1

| | |
|---|---|
| 0.2 M · Tris-HCl buffer (PH 8.0) | 0.2 ml |
| 10 mM CoA | 0.05 ml |
| 0.2 mM · 3-oxopalmitoyl CoA | 0.1 ml |
| 100 mM · MgCl$_2$ | 0.1 ml |
| 1 mM · Dithiothreitol | 0.1 ml |
| Distilled water | 0.45 ml |
| Total | 1.00 ml |

In order to acquire bacterium for producing polyhydroxyalkanoate characterized in that the gene encoding acetyl-CoA acyltransferase is disrupted by selective gene disruption, a method using homologous recombination with a linear DNA can be used, but damages of the bacteria can be reduced particularly by using targeting vector for an acetyl-CoA acyltransferase gene disclosed in one of the invention of this application and polyhydroxyalkanoate producing bacteria in which the gene is disrupted can be acquired effectively.

Figure 5A:
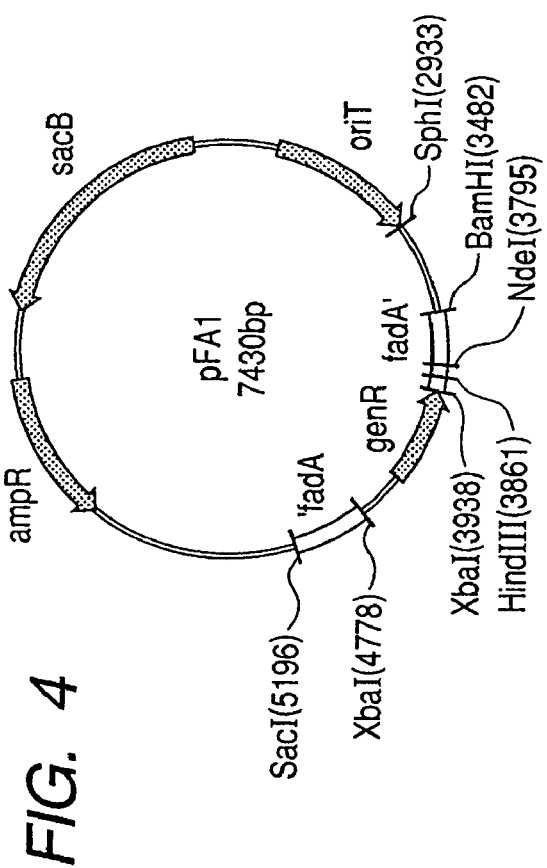
FIGS. 5A and 5B illustrate processes of selective gene-disruption by gene insertion disruption method and gene substitution disruption method.
Figure 5B:
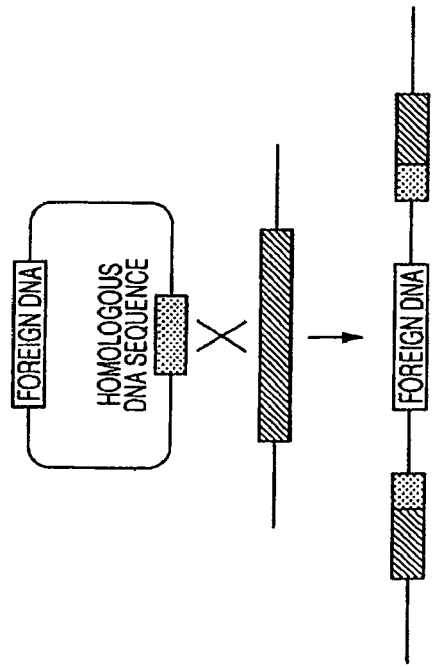

Generally, selective gene disruption method by homologous recombination to the target site in the chromosome is used in the research for elucidation of the gene function and to selectively disrupt the gene concerned with undesirable character in breeding of practical bacterial strain, and two types of methods, gene insertion disruption method and gene substitution disruption method are used for selective gene disruption (FIGS. 5A and 5B). Each of these methods has a basic principle of incorporating the desired exogenous gene contained in an exogenous targeting DNA into the target DNA sequence of the endogenous genomic DNA by artificially causing homologous recombination of genes, which can naturally occur in a living body of an organism, between the endogenous genomic DNA present on the chromosome of the organism and the exogenous targeting DNA (targeting vector). Either method of the above-mentioned gene insertion disruption method and the above-mentioned gene substitution disruption method can be used to produce the bacterium for producing polyhydroxyalkanoate of the present invention characterized in that the gene encoding acetyl-CoA acyltransferase is disrupted.

The gene targeting vector in the present invention means a DNA structure which is used to disrupt a gene encoding the target DNA (acetyl-CoA acyltransferase) in the endogenous genomic DNA of bacterium for producing polyhydroxyalkanoate by homologous recombination. The term "disruption" (gene disruption) as used herein means a modification of the DNA sequence as described below which is introduced into a part of the endogenous genome by homologous recombination between the targeting DNA and endogenic genomic DNA.

(1) Deletion of a part of DNA sequence of the target DNA (2) Substitution of a part of DNA sequence of the target DNA with an exogenous DNA (3) Insertion of an exogenous DNA into the target DNA sequence.

The modification of the DNA sequence achieved by insertion gene insertion disruption method is a modification by the above-mentioned (3) and the modification of the DNA sequence achieved by gene substitution disruption method is a modification by the above-mentioned (1), (2) or (3). The gene encoding acetyl-CoA acyltransferase in the endogenic genomic DNA of a bacterium for producing polyhydroxyalkanoate substantially loses the function by these modifications, and transcription and translation of the acetyl-CoA acyltransferase gene or biosynthesis of acetyl-CoA acyltransferase protein maintaining activity can be prevented.

The basic structure of the targeting vector for an acetyl-CoA acyltransferase gene of the present invention is different depending on the type of gene disruption technique and can take the following three basic structures.

(I) A structure basically composed of DNA represented by the following (a) or (b) or a part thereof and a part for desired gene disruption which are linked by a vector,
(a) a DNA comprising a base sequence shown in SEQ ID NO: 1,
(b) a DNA which hybridizes with a DNA consisting of a base sequence complementary to the base sequence shown in SEQ ID NO: 1 under stringent conditions.

(II) When the target gene is disrupted by gene insertion disruption method, the gene targeting vector of the present invention comprises the following DNA sequences shown by the following (a) or (b) or a part thereof as a DNA sequence homologous to the target gene (homologous region):
(a) a DNA comprising a base sequence shown in SEQ ID NO: 1,
(b) a DNA which hybridizes with a DNA consisting of a base sequence complementary to the base sequence shown in SEQ ID NO: 1 under stringent conditions, and has a basic structure having a desired exogenous DNA foreign to the endogenous genomic DNA.

(III) When the target gene is disrupted by gene substitution disruption method, the gene targeting vector of the present invention comprises the following DNA sequences shown by the following (a) or (b) or a part thereof as a DNA sequence homologous to the target gene (homologous region):
(a) a DNA comprising a base sequence shown in SEQ ID NO: 1,
(b) a DNA which hybridizes with a DNA consisting of a base sequence complementary to the base sequence shown in SEQ ID NO: 1 under stringent conditions, and has a basic structure having inserted a desired exogenous DNA foreign to the endogenous genomic DNA in the DNA sequence homologous to the target gene (homologous region).

Here, the DNA "which hybridizes . . . under stringent conditions" in the basic structures (I), (II) and (III) refers to the following DNA. That is, it refers to a DNA (1) which forms a DNA-DNA hybrid with a DNA comprising a base sequence shown in SEQ ID NO: 1 by hybridizing in a high ion concentration (for example, 6×SSC (900 mM of sodium chloride, 90 mM of sodium citrate) can be exemplified.) at a temperature condition of 65° C. and (2) and maintains the DNA-DNA hybrid after washed in a low ion concentration (for example, 0.1×SSC (15 mM of sodium chloride, 1.5 mM of sodium citrate) can be exemplified.) at a temperature condition of 65° C. for 30 minutes. Specific examples thereof include a DNA comprising a base sequence in which a part of the base sequence is deleted, substituted or added in the base sequence shown in SEQ ID NO: 1 in the range which allows to maintain the desired gene disruption function. Such a DNA may be a DNA cloned from nature, or deletion, substitution or addition of base is artificially introduced into a DNA cloned from nature, or may be an artificially synthesized DNA. In addition, "DNA sequences shown by the following (a) or (b) or a part thereof" in the constitutional elements (I), (II) and (III) does not have to encode a protein having acetyl-CoA acyltransferase activity and it suffices that the DNA has such a homology that it can cause homologous recombination with the acetyl-CoA acyltransferase gene in the chromosome under a physiological condition, namely, in a microbial cell, and thereby can disrupt the acetyl-CoA acyltransferase gene. Such a homology includes preferably the homology of 90% or more, more preferably the homology of 95% or more. In addition, the DNA to be used for producing a disrupted strain of acetyl-CoA acyltransferase gene may be a part of DNA of the present invention as long as it can cause homologous recombination with the acetyl-CoA acyltransferase gene in the chromosome and has a size sufficient to thereby disrupt acetyl-CoA acyltransferase gene. Here, the term "a part" refers to a length preferably having 50 bases or more, more preferably 100 bases or more and may include a part having a desired gene disruption function.

If "a part" of the DNA represented by (a) or (b) is exemplified as a specific sequence to be provided in the gene targeting vector, it includes SEQ ID NO: 11, SEQ ID NO: 12, SEQ ID NO: 13, SEQ ID NO: 14 and SEQ ID NO: 15.

The vector in the basic structure (I) is not particularly limited, but common wide range host vector, for example, pJRD215 (Davidson et al., Gene, 51., 275-280 (1987)) can be used and the pBBRIMCS series (Kovach et al., Gene. 166, 175-176 (1995)), etc. can be exemplified.

Examples of the "exogenous DNA" in the basic structure (II) and (III) include a marker gene, a reporter gene, a gene amplifying gene, a gene expression control DNA sequence which I can add such characteristics as leading to substantial break down of acetyl-CoA acyltransferase gene by deletion, substitution or insertion to the target DNA sequence in the endogenic genomic DNA or a DNA sequence containing one or more of them. Here, any kind of used marker gene usually used in the technical field of gene recombination can be used as a "marker gene". For example, resistant genes for antibiotics such as tetracycline, ampicillin, gentamicin or kanamycin are exemplified. Genes such as luciferase and green fluorescence protein (GFP), β-lactamase are exemplified as a "reporter gene". Further, DNA sequences having a desired primer linked sequence which enables to obtain specific gene amplification products of the disrupted strain by PCR method using the chromosome DNA as a template are exemplified as a gene amplifying gene.

The gene targeting vector of the basic structure (II) and (III) containing a Mob site containing the origin of conjugation (OriT) enables effective transduction to bacterium for producing polyhydroxyalkanoate, for example, when transformed into an *Escherichia coli* mobilizer strain (for example, S17-1 strain (ATCC 47055)) and used as a plasmid donor, and it reduces damage to the bacterium for producing polyhydroxyalkanoate and enables to more effectively and easily obtain a strain in which acetyl-CoA acyltransferase gene is disrupted, and therefore, it is more preferable. This is because the gene targeting vector of mob+, tra− in conjugative transfer can be conjugatively transfered without help by a helper plasmid since *Escherichia coli* mobilizer strain has tra gene (R. Simon et al. (1983) Bio-Technology 1: 784).

It is desirable to allow the gene targeting vector of the basic structure (III) to contain a gene (sensitive gene) which leads plasmid recipient bacterium to lethality under a certain condition. As for the sensitive gene, it has been found that, for example, levansucrase, sacB derived from *Buccilus subtilis* leads most of the gram-negative bacteria to lethality in a culture medium containing sucrose 5% by weight or more (Gay et al., J. Bacteriol. 164, 918), and it has been confirmed that it also functions in *Pseudomonas* sp. YN21 strain by the inventors, and therfore it can be suitably used in the present invention.

In the gene targeting vector of the basic structure (III), insertion site of DNA represented by the above (a) or (b) or a part thereof into the selection marker is from 1 to 9, preferably from 2 to 8, more preferably from 4 to 6 assuming the length of DNA represented by the above (a) or (b) or a part thereof incorporated into the vector to be 10. If the insertion site of the selection marker is disproportionately near the end of the DNA shown by the above (a) or (b) or a part thereof, the acquisition efficacy of double homologous recombinant using the effect of the sensitivite gene decreases and such a case is unfavorable.

In order to construct a gene targeting vector of the basic structure (I), (II) or (III), each DNA which is a constituting element of the above-mentioned basic structure may be incorporated into the vector using conventional molecular technique but a mobile vector provided with a replicant gene having incompatibility with the replicant gene possessed by the bacterium for producing polyhydroxyalkanoate, an origin of conjugation and a sensitive gene beforehand is useful because the targeting vector of acetyl-CoA acyltransferase gene of the present invention can be prepared by a shoter process. Examples of such a mobile vector include pEX100T (ATCC 87436), pJQ200 (ATCC 77482), pDMS197 (ATCC 87694), pRE107 (ATCC 87691) and they can be preferably used for constructing the targeting vector for an acetyl-CoA acyltransferase gene of the present invention.

For example, in order to construct the gene targeting vector of the basic structure (III), the DNA represented by the above (a) or (b) or a part thereof and a selection marker may be incorporated into the vector. There is not restriction in the order of incorporating these but as an example of the procedure, a suitable restriction enzyme is allowed to act on the above mobile vector at first and the resulted vector DNA fragments are mixed with the above (a) or (b) or a part thereof and a DNA ligase is allowed to act on them. Then a restriction enzyme which cleaves the restriction site different from the above restriction enzyme is allowed to act, and a part of the above vector or the DNA represented by the above (a) or (b) or a part thereof is cleaved. The resulted vector DNA fragments are mixed with the DNA fragment containing the selection marker and a selection marker is inserted by acting a DNA ligase on this mixture. If necessary, procedures known in the art such as addition of a linker, blunt end treatment can be added in the above-mentioned process.

In order to disrupt the acetyl-CoA acyltransferase gene of a bacterium for producing polyhydroxyalkanoate with a gene targeting vector of the basic structure (I), the gene targeting vector is introduced into the bacterium for producing polyhydroxyalkanoate. The method to introduce the gene targeting vector can be appropriately selected and used among the methods well known to those skilled in the art such as a method of contacting with a competent cell and electroporation-method. The first screening is then performed, for example, utilizing the property that they cannot grow on an agar plate containing a fatty acid as single carbon source and the acquired clones are checked whether the gene of acetyl-CoA acyltransferase is disrupted.

In order to disrupt the acetyl-CoA acyltransferase gene of a bacterium for producing polyhydroxyalkanoate with a gene targeting vector of the basic structure (II) or (III), the same procedure can be performed as in the case of using the gene targeting vector of the basic structure (I), but at first the targeting vector is transformed into the above mobilizer strain of *Escherichia coli*. The gene targeting vector is then transferred to the bacterium for producing polyhydroxyalkanoate body utilizing conjugal transfer between the transformed mobilizer strain of *Escherichia coli* and a bacterium for producing polyhydroxyalkanoate.

As a result of homologous recombination with the gene targeting vector and chromosome DNA, the strains in which the acetyl-CoA acyltransferase gene is disrupted can be acquired by selecting with the above selection marker. There are two homologous sites in the chromosome of the host bacterium for producing polyhydroxyalkanoate and the gene targeting vector before and after the above selection marker, and therefore most of the homologous recombinants obtained at this stage are two kinds of recombinants different from each other having chromosome structures in which the sequence derived from the gene targeting vector is inserted into the different sites, and it is considered that the ratio of the homologous recombinant is very little in which crossing over has occurred at the two homologous sites of selection marker before and after the selection marker at the same time. The acetyl-CoA acyltransferase gene is disrupted by the insertion of the sequence derived from the gene targeting vector.

When a gene targeting vector of the basic structure (III) is used, selection based on sensitive genetic function is subsequently performed. This selection enables to acquire the mutant in which the mobile vector site is deleted from the sequence derived from the gene targeting vector which have been inserted in the chromosome of the recombinant selected from among the plasmid recipient bacteria with the above selection marker. This is performed by homologous recombination at the other homologous site which has not been used in the homologous recombination of the preceding step. Therefore, the two kinds of the recombinants having different chromosome structures at the preceding step become a recombinant of the same chromosome structure (in which the acetyl-CoA acyltransferase gene is divided by the selection marker) at this stage.

The fact that the acetyl-CoA acyltransferase gene is disrupted in the recombinant acquired with the acetyl-CoA acyltransferase enzyme gene targeting vector of the present invention can be confirmed by confirming disappearance of acetyl-CoA acyltransferase activity of bacteria fragmented liquid of recombinant by the above-mentioned method, by using Southern hybridization method after cleaving the chromosome DNA of the recombinant with a restriction enzyme, or by using PCR method with suitable primers and so on.

The targeting vector for an acetyl-CoA acyltransferase gene of the present invention autonomously replicates and amplifies itself in a suitable host cell, and therefore, copies of this vector can be produced by culturing the transformant which has been obtained by introducing this vector into the host cell and performing genetic transformation. Any host cell can be used as such a host cell without discrimination of gram-negative bacteria or gram-positive bacteria, cells of lower organism or higher organism, plant origin cell or animal origin cell, as long as it can be transformed with the targeting vector for an acetyl-CoA acyltransferase gene obtained as above and can stably maintain and replicate this vector. In order to introduce the gene targeting vector into the host cell, methods can be appropriately selected and used among the methods well known to those skilled in the art such as a method of contacting with a competent cell and electroporation method.

Culture media containing ingredients necessary for the replication of disrupted strain to be used can be appropriately selected and used for usual cultivation of the acetyl-CoA acyltransferase gene disrupted strain to be used in the process for producing PHA according to the present invention, for example, for preparing a stock strain and for replication to secure the number of bacteria and active state needed for the production of PHA. For example, any type of culture media can be used such as common natural media (nutrient broth, yeast extract, etc.) and synthetic culture media to which nutrient sources are added unless they do not have bad influence on the growth and survival of the disrupted strain.

Any type of culturing method such as liquid culturing and solid culturing can be used as long as it allows the disrupted strain to replicate and produce PHA. The type of culturing such as batch culturing, fed batch culturing, semicontinuous culturing, continuous culturing does not matter, either. The embodiment of the liquid batch culturing includes a method of shaking with a shaking flask to thereby supply oxygen, an oxygen supplying method by agitation aeration in a jar fermenter. Multistage methods in which two or more of these steps are connected may be adopted.

The composition and structure of PHA which can be produced with the acetyl-CoA acyltransferase gene disrupted strain, particularly the type of unusual PHA having a substituent group in the side chain can be defined by the characteristics of the acetyl-CoA acyltransferase gene non-disrupted strain which is an isogenic strain thereof, and when *Pseudomonas* sp. FA1 strain which is an isogenic strain of *Pseudomonas* sp. YN21 strain and which is a bacterium for producing polyhydroxyalkanoate with disrupted acetyl-CoA acyltransferase gene is used, polyhydroxyalkanoate characterized by containing at least one kind of the polymer units selected from the group consisting of the polymer units, for example, those represented by the following chemical formulae (1) to (16) in the polymer molecule can be produced.

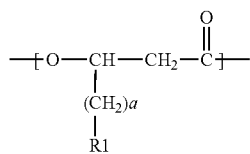
(1)

(wherein the polymer unit is at least one selected from the group consisting those in which the combination of R1 and a is either one of the following:
(1) a polymer unit in which R1 is a hydrogen atom (H) and a is any of integers from 1 to 10,
(2) a polymer unit in which R1 is a halogen atom and a is any of integers from 1 to 10,
(3) a polymer unit in which R1 is

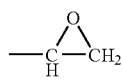

and a is any of integers from 1 to 8.)

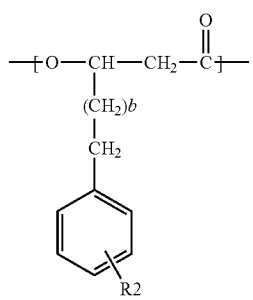
(2)

(wherein R2 represents a substituent group to the aromatic ring, and R2 represents either one selected from the group consisting of a hydrogen atom (H), a halogen atom, CN group, $NO_2$ group, COOR' (R': representing either one of H, Na and K) group, $CH_3$ group, $C_2H_5$ group, $C_3H_7$ group, $CH=CH_2$ group, $CF_3$ group, $C_2F_5$ group and $C_3F_7$ group, and b represents any of integers from 0 to 7).

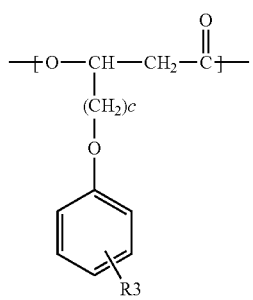
(3)

(wherein R3 represents a substituent group to the aromatic ring, and R3 represents either one selected from the group consisting of a hydrogen atom (H), a halogen atom, CN group, $NO_2$ group, $CH_3$ group, $C_2H_5$ group, $C_3H_7$ group, $SCH_3$ group, $CF_3$ group, $C_2F_5$ group and $C_3F_7$ group, and c represents any of integers from 0 to 7).

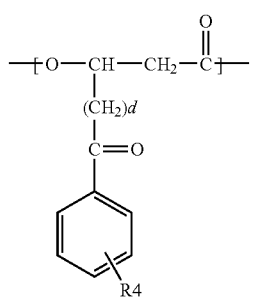
(4)

(wherein R4 represents a substituent group to the aromatic ring, and R4 represents either one selected from the group consisting of a hydrogen atom (H), a halogen atom, CN group, $NO_2$ group, $CH_3$ group, $C_2H_5$ group, $C_3H_7$ group, $CF_3$ group, $C_2F_5$ group and $C_3F_7$ group, and d represents any of integers from 0 to 7).

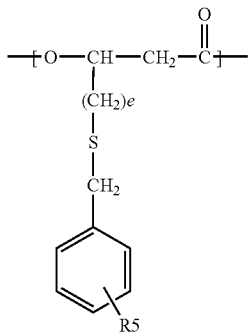

(5)

(wherein R5 represents a substituent group to the aromatic ring, and R5 represents either one selected from the group consisting of a hydrogen atom (H), a halogen atom, CN group, $NO_2$ group, COOR' (R': representing either one of H, Na, K, $CH_3$ and $C_2H_5$) group, $SO_2R''$ (R'': representing either one of OH, ONa, OK, a halogen atom, $OCH_3$ and $OC_2H_5$) group, $CH_3$ group, $C_2H_5$ group, $C_3H_7$ group, $CH(CH_3)_2$ group and $C(CH_3)_3$ group, and e represents any of integers from 1 to 8).

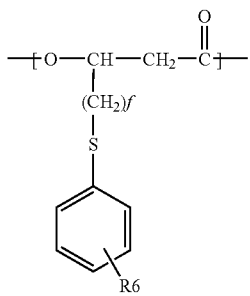

(6)

(wherein R6 represents a substituent group to the aromatic ring, and R6 represents either one selected from the group consisting of a hydrogen atom (H), a halogen atom, CN group, $NO_2$ group, COOR' (R': representing either one of H, Na, K, $CH_3$ and $C_2H_5$) group, $SO_2R''$ (R'': representing either one of OH, ONa, OK, a halogen atom, $OCH_3$ and $OC_2H_5$) group, $CH_3$ group, $C_2H_5$ group, $C_3H_7$ group, $CH(CH_3)_2$ group and $C(CH_3)_3$ group, and f represents any of integers from 1 to 8).

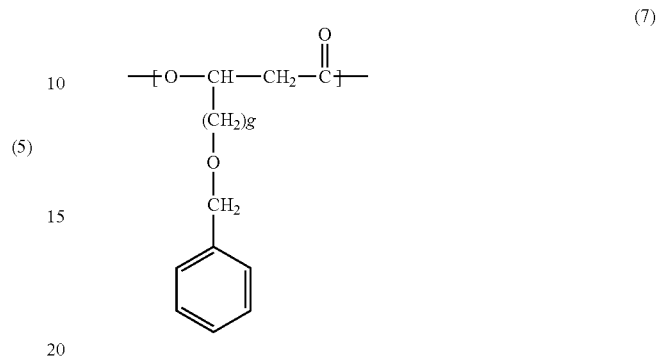

(7)

(wherein g represents any of integers from 1 to 8.)

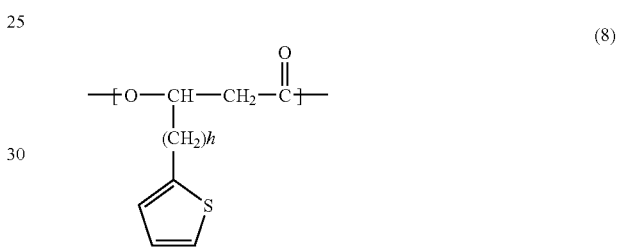

(8)

(wherein h represents any of integers from 1 to 8.)

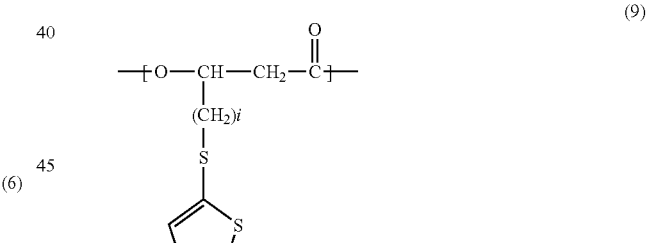

(9)

(wherein i represents any of integers from 1 to 8.)

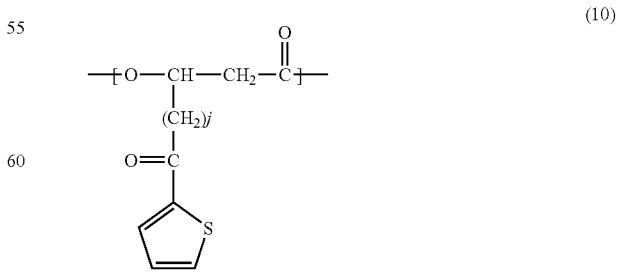

(10)

(wherein j represents any of integers from 1 to 8.)

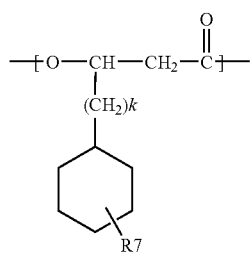
(11)

(wherein R7 represents a substituent group to the cyclohexyl group, and R7 represents either one selected from the group consisting of a hydrogen atom (H), a halogen atom, CN group, $NO_2$ group, $CH_3$ group, $C_2H_5$ group, $C_3H_7$ group, $CF_3$ group, $C_2F_5$ group and $C_3F_7$ group, and k represents any of integers from 0 to 8).

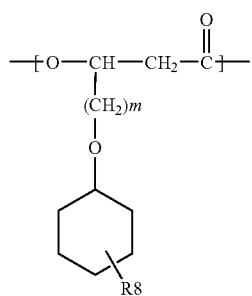
(12)

(wherein R8 represents a substituent group to the cyclohexyl group, and R8 represents either one selected from the group consisting of a hydrogen atom (H), a halogen atom, CN group, $NO_2$ group, $CH_3$ group, $C_2H_5$ group, $C_3H_7$ group, $CF_3$ group, $C_2F_5$ group and $C_3F_7$ group, and m represents any of integers from 0 to 8).

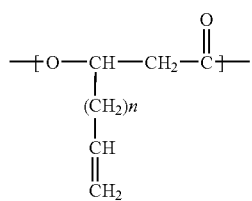
(13)

(wherein n represents any of integers from 1 to 8.)

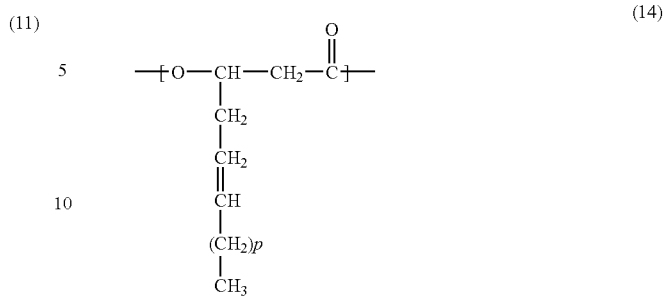
(14)

(wherein p represents an either integer of 3 or 5.)

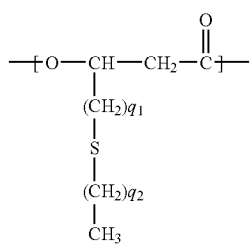
(15)

(wherein $q_1$ represents any of integers from 1 to 8, and $q_2$ represents any of integers from 0 to 8.)

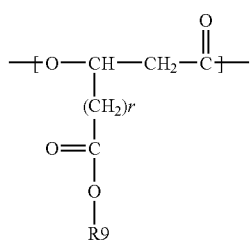
(16)

(wherein R9 is a hydrogen atom (H), Na atom or K atom, and r represents any of integers from 1 to 8.)

When PHA containing 3-hydroxyalkanoic acid unit as a monomer unit is produced with an acetyl-CoA acyltransferase gene disrupted strain, inorganic media which at least contain respectively corresponding alkanoic acid or alkane as raw materials of PHA production and carbon source for replication of the disrupted strain can be used. As for the carbon source for replication, medium ingredients derived from natural product such as yeast extract, polypeptone, meat extract, casamino acid can be used and saccharides, organic acids participating in TCA cycle (organic acids produced as intermediate products in TCA cycle and organic acids produced through one-step or two-step biochemical reaction from TCA cycle) or the salt thereof and any kind of compound producing acetyl-CoA without passing through β-oxidation cycle can be used and they can be appropriately selected depending on the availability as a substrate for the strain to be used. Two or more compounds can be also selected and used as long as they are a combination which causes little contamination of mcl-3HA.

Of these, one or more compounds can be preferably used for saccharide including aldose such as glyceraldehyde, erythrose, arabinose, xylose, glucose, galactose, mannose and fructose, alditol such as glycerol, erythritol and xylitol, aldonic acid such as gluconic acid, uronic acid such as glucuronic acid and galacturonic acid, and disaccharide such as maltose, sucrose and lactose.

As for the organic acid or the salt thereof, pyruvic acid, oxalacetic acid, citric acid, isocitric acid, ketoglutaric acid, succinic acid, fumaric acid, malic acid, lactic acid are the examples and one or more compounds selected from the salts thereof can be preferably used.

Among these, saccharide is particularly preferably used, and in particular, at least one selected from the group consisting of glucose, fructose and mannose is more preferable. The method for producing and accumulating PHA in microorganisms may be performed by once allowing the replication sufficiently, transferring the bacterial cell to a culture medium in which nitrogen source such as ammonium chloride is limited, and further culturing in a state that a compound which will be the substrate of the purpose unit is added, in which process the productivity may be improved. Specifically, adoption of the multistage method in which two or more of the above steps are connected can be exemplified. For example, there is a process which comprises performing culturing from the late logarithmic growth phase to stationary growth phase in an inorganic medium containing about 0.05 wt % to 5.0 wt % of D-glucose, about 0.01 wt % to 1.0 wt % of alkanoic acid or alkane, collecting bacterial cells by centrifugal separation and then further culturing in an inorganic medium containing about 0.01 wt % to 1.0 wt % of alkanoic acid or alkane in which nitrogen source is limited or not substantially absent.

Any inorganic medium can be used for the culture method mentioned above, as long as it contains ingredients such as phosphorous source (for example, phosphate), nitrogen source (for example, ammonium salt, nitrate) to allow the microorganism to replicate and examples of the inorganic salt culture medium include MSB culture medium, E culture medium (J. Biol. Chem., 218, 97-106 (1956)), M9 culture medium.

The composition of M9 culture medium used in the Examples of the present invention is as follows.

$Na_2HPO_4$: 6.2 g
$KH_2PO_4$: 3.0 g
NaCl: 0.5 g
$NH_4Cl$: 1.0 g (per 1 liter of culture medium, PH7)

It is preferable to add a solution of the following trace elements to the culture medium of the above inorganic salt culture medium in an amount of about 0.3% (v/v) for better replication and production of PHA.

Trace Element Solution
nitrilotriacetic acid: 1.5 g
$MgSO_4$: 3.0 g
$MnSO_4$: 0.5 g
NaCl: 1.0 g
$FeSO_4$: 0.1 g
$CaCl_2$: 0.1 g
$COCl_2$: 0.1 g
$ZnSO_4$: 0.1 g
$CuSO_4$: 0.1 g
$AlK(SO_4)_2$: 0.1 g
$H_3BO_3$: 0.1 g
$Na_2MoO_4$: 0.1 g
$NiCl_2$: 0.1 g (In 1 liter)

Culturing temperature may be a temperature in which the strain mentioned above can replicate well, and, for example, 15 to 40° C., preferably 20 to 35° C., and most preferably about 20° C. to 30° C.

As a specific example, desired PHA containing little or no monomer unit other than the purpose monomer unit can be extracted by culturing in an inorganic medium containing about 0.05 wt % to 5.0 wt % of D-glucose and about 0.01 wt % to 1.0 wt % of alkanoic acid or alkane, and collecting the bacterial cells from the late logarithmic growth phase to stationary growth. Such PHA generally consists of only R-configuration, and it is an isotactic polymer.

An organic acid participating in TCA cycle, yeast extract or polypeptone may be added in substitution for D-glucose. These can be used in combination as well.

PHA can be acquired from the culture broth of the present invention by applying usually performed methods. When PHA is secreted to the culture broth, an extraction purification method from the culture broth is used and when it is accumulated in the bacterial cells, an extraction purification method from the bacterial cells is used. For example, extraction with an organic solvent such as chloroform, which is usually performed, is the most simple for collecting PHA from the culture body of bacteria, but there may be used dioxane, tetrahydrofuran, acetonitrile, acetone besides chloroform. In the environment where it is hard to use an organic solvent, bacterial cell components other than PHA are removed by treatment with a surfactant such as SDS, treatment with an enzyme such as lysozyme, treatment with a chemical agent such as EDTA and a method for collecting PHA can be used.

Culturing a microorganism of the present invention, production and accumulation to bacterial cells of PHA by a microorganism of the present invention and recovery of PHA from the bacterial cells are not limited to the method mentioned above.

When the bacterium for producing polyhydroxyalkanoate provided by the present invention characterized in that the gene encoding acetyl-CoA acyltransferase is disrupted is cultured in a culture medium to which fatty acids are added, releasing of acetyl-CoA and new generation of a substrate (acyl-CoA) having a chain length shortened by two methylene chains are halted in the β-oxidation system of fatty acid because acetyl-CoA acyltransferase is disrupted, and intracellular accumulation of 3-oxoacyl-CoA, 3-hydroxyacyl-CoA or trans-2,3-dehydroacyl-CoA which are metabolic intermediates of β-oxidation system is caused and therefore, it can be preferably used for producing these fatty acid metabolic intermediates. Particularly, when *Pseudomonas* sp. FA1 strain which is an isogenic strain of *Pseudomonas* sp. YN21 strain and which is a bacterium for producing polyhydroxyalkanoate with disrupted acetyl-CoA acyltransferase gene is used, 3-oxoacyl-CoA, for example, those represented by the following chemical formulae (17) to (32) can be produced.

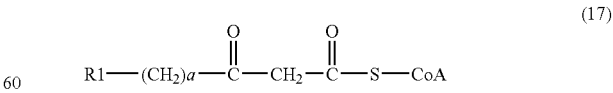
(17)

(wherein the 3-oxoacyl-CoA is at least one selected from the group consisting those in which the combination of R1 and a is either one of the following:

(1) 3-oxoacyl-CoA in which R1 is a hydrogen atom (H) and a is any of integers from 1 to 10, (2) 3-oxoacyl-CoA in which R1 is a halogen atom and a is any of integers from 1 to 10,
(3) 3-oxoacyl-CoA in which R1 is

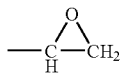

and a is any of integers from 1 to 8.)

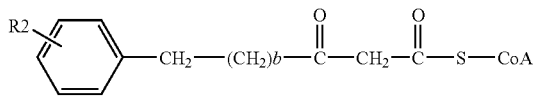
(18)

(wherein R2 represents a substituent group to the aromatic ring, and R2 represents either one selected from the group consisting of a hydrogen atom (H), a halogen atom, CN group, $NO_2$ group, COOR' (R': representing either one of H, Na and K) group, $CH_3$ group, $C_2H_5$ group, $C_3H_7$ group, $CH=CH_2$ group, $CF_3$ group, $C_2F_5$ group and $C_3F_7$ group, and b represents any of integers from 0 to 7).

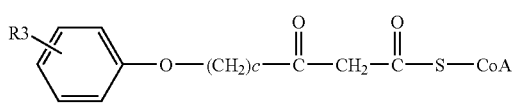
(19)

(wherein R3 represents a substituent group to the aromatic ring, and R3 represents either one selected from the group consisting of a hydrogen atom (H), a halogen atom, CN group, $NO_2$ group, $CH_3$ group, $C_2H_5$ group, $C_3H_7$ group, $SCH_3$ group, $CF_3$ group, $C_2F_5$ group and $C_3F_7$ group, and c represents any of integers from 0 to 7).

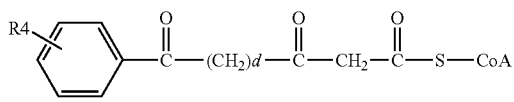
(20)

(wherein R4 represents a substituent group to the aromatic ring, and R4 represents either one selected from the group consisting of a hydrogen atom (H), a halogen atom, CN group, $NO_2$ group, $CH_3$ group, $C_2H_5$ group, $C_3H_7$ group, $CF_3$ group, $C_2F_5$ group and $C_3F_7$ group, and d represents any of integers from 0 to 7).

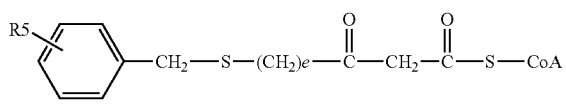
(21)

(wherein R5 represents a substituent group to the aromatic ring, and R5 represents either one selected from the group consisting of a hydrogen atom (H), a halogen atom, CN group, $NO_2$ group, COOR' (R': representing either one of H, Na, K, $CH_3$ and $C_2H_5$) group, $SO_2R''$ (R'': representing either one of OH, ONa, OK, a halogen atom, $OCH_3$ and $OC_2H_5$) group, $CH_3$ group, $C_2H_5$ group, $C_3H_7$ group, $CH(CH_3)_2$ group and $C(CH_3)_3$ group, and e represents any of integers from 1 to 8).

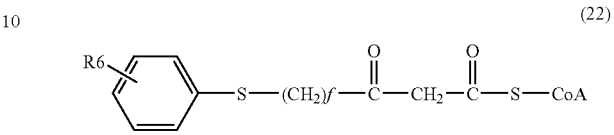
(22)

(wherein R6 represents a substituent group to the aromatic ring, and R6 represents either one selected from the group consisting of a hydrogen atom (H), a halogen atom, CN group, $NO_2$ group, COOR' (R': representing either one of H, Na, K, $CH_3$ and $C_2H_5$) group, $SO_2R''$ (R'': representing either one of OH, ONa, OK, a halogen atom, $OCH_3$ and $OC_2H_5$) group, $CH_3$ group, $C_2H_5$ group, $C_3H_7$ group, $CH(CH_3)_2$ group and $C(CH_3)_3$ group, and f represents any of integers from 1 to 8).

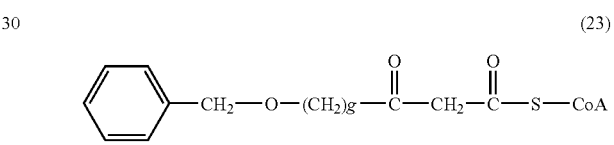
(23)

(wherein g represents any of integers from 1 to 8.)

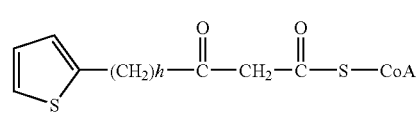
(24)

(wherein h represents any of integers from 1 to 8.)

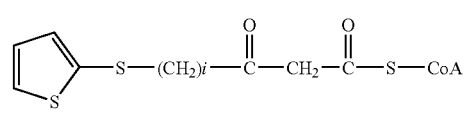
(25)

(wherein i represents any of integers from 1 to 8.)

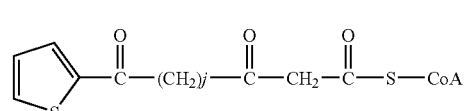
(26)

(wherein j represents any of integers from 1 to 8.)

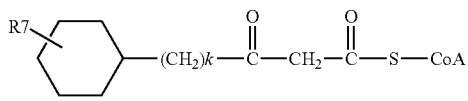
(27)

(wherein R7 represents a substituent group to the cyclohexyl group, and R7 represents either one selected from the group consisting of a hydrogen atom (H), a halogen atom, CN group, $NO_2$ group, $CH_3$ group, $C_2H_5$ group, $C_3H_7$ group, $CF_3$ group, $C_2F_5$ group and $C_3F_7$ group, and k represents any of integers from 0 to 8).

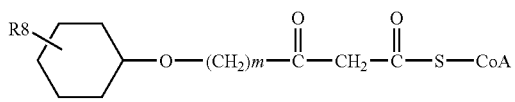
(28)

(wherein R8 represents a substituent group to the cyclohexyl group, and R8 represents either one selected from the group consisting of a hydrogen atom (H), a halogen atom, CN group, $NO_2$ group, $CH_3$ group, $C_2H_5$ group, $C_3H_7$ group, $CF_3$ group, $C_2F_5$ group and $C_3F_7$ group, and m represents any of integers from 0 to 8).

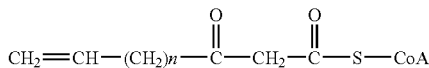
(29)

(wherein n represents any of integers from 1 to 8.)

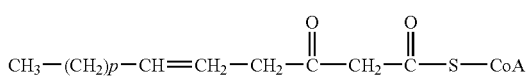
(30)

(wherein p represents an either integer of 3 or 5.)

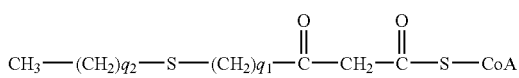
(31)

(wherein $q_1$ represents any of integers from 1 to 8, and $q_2$ represents any of integers from 0 to 8.)

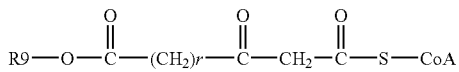
(32)

(wherein R9 is a hydrogen atom (H), Na atom or K atom, and r represents any of integers from 1 to 8.) In addition, when *Pseudomonas* sp. FA1 strain which is a bacterium for producing polyhydroxyalkanoate is used, 3-hydroxyacyl-CoA, for example, those represented by the following chemical formulae (33) to (48) can be produced.

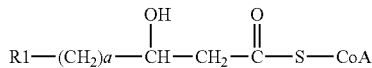
(33)

(wherein the 3-hydroxyacyl-CoA is at least one selected from the group consisting those in which the combination of R1 and a is either one of the following:
(1) 3-hydroxyacyl-CoA in which R1 is a hydrogen atom (H) and a is any of integers from 1 to 10,
(2) 3-hydroxyacyl-CoA in which R1 is a halogen atom and a is any of integers from 1 to 10,
(3) 3-hydroxyacyl-CoA in which R1 is

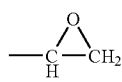

and a is any of integers from 1 to 8.)

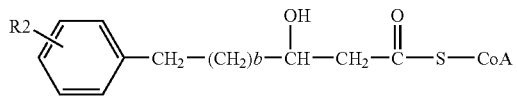
(24)

(wherein R2 represents a substituent group to the aromatic ring, and R2 represents either one selected from the group consisting of a hydrogen atom (H), a halogen atom, CN group, $NO_2$ group, COOR' (R': representing either one of H, Na and K) group, CH3 group, $C_2H_5$ group, $C_3H_7$ group, $CH=CH_2$ group, $CF_3$ group, $C_2F_5$ group and $C_3F_7$ group, and b represents any of integers from 0 to 7).

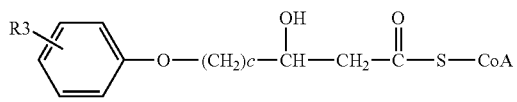
(35)

(wherein R3 represents a substituent group to the aromatic ring, and R3 represents either one selected from the group consisting of a hydrogen atom (H), a halogen atom, CN group, $NO_2$ group, $CH_3$ group, $C_2H_5$ group, $C_3H_7$ group, $SCH_3$ group, $CF_3$ group, $C_2F_5$ group and $C_3F_7$ group, and c represents any of integers from 0 to 7).

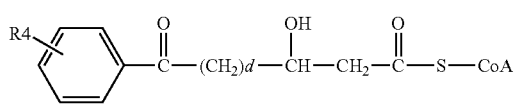
(36)

(wherein R4 represents a substituent group to the aromatic ring, and R4 represents either one selected from the group consisting of a hydrogen atom (H), a halogen atom, CN group, NO₂ group, CH₃ group, C₂H₅ group, C₃H₇ group, CF₃ group, C₂F₅ group and C₃F₇ group, and d represents any of integers from 0 to 7).

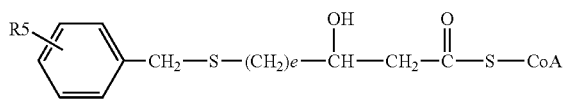
(37)

(wherein R5 represents a substituent group to the aromatic ring, and R5 represents either one selected from the group consisting of a hydrogen atom (H), a halogen atom, CN group, NO₂ group, COOR' (R': representing either one of H, Na, K, CH₃ and C₂H₅) group, SO₂R" (R": representing either one of OH, ONa, OK, a halogen atom, OCH₃ and OC₂H₅) group, CH₃ group, C₂H₅ group, C₃H₇ group, CH(CH₃)₂ group and C(CH₃)₃ group, and e represents any of integers from 1 to 8).

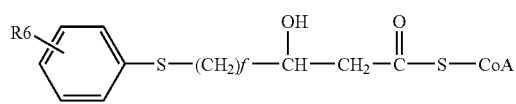
(38)

(wherein R6 represents a substituent group to the aromatic ring, and R6 represents either one selected from the group consisting of a hydrogen atom (H), a halogen atom, CN group, NO₂ group, COOR' (R': representing either one of H, Na, K, CH₃ and C₂H₅) group, SO₂R" (R": representing either one of OH, ONa, OK, a halogen atom, OCH₃ and OC₂H₅) group, CH₃ group, C₂H₅ group, C₃H₇ group, CH(CH₃)₂ group and C(CH₃)₃ group, and f represents any of integers from 1 to 8).

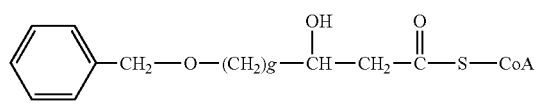
(39)

(wherein g represents any of integers from 1 to 8.)

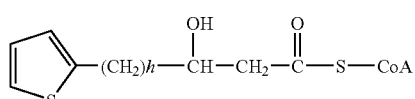
(40)

(wherein h represents any of integers from 1 to 8.)

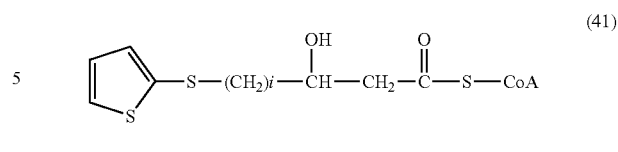
(41)

(wherein i represents any of integers from 1 to 8.)

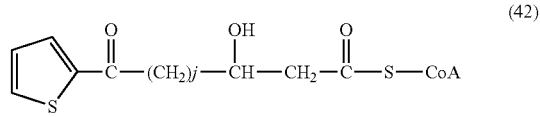
(42)

(wherein j represents any of integers from 1 to 8.)

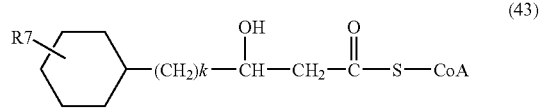
(43)

(wherein R7 represents a substituent group to the cyclohexyl group, and R7 represents either one selected from the group consisting of a hydrogen atom (H), a halogen atom, CN group, NO₂ group, CH₃ group, C₂H₅ group, C₃H₇ group, CF₃ group, C₂F₅ group and C₃F₇ group, and k represents any of integers from 0 to 8).

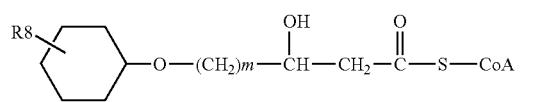
(44)

(wherein R8 represents a substituent group to the cyclohexyl group, and R8 represents either one selected from the group consisting of a hydrogen atom (H), a halogen atom, CN group, NO₂ group, CH₃ group, C₂H₅ group, C₃H₇ group, CF₃ group, C₂F₅ group and C₃F₇ group, and m represents any of integers from 0 to 8).

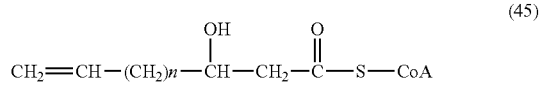
(45)

(wherein n represents any of integers from 1 to 8.)

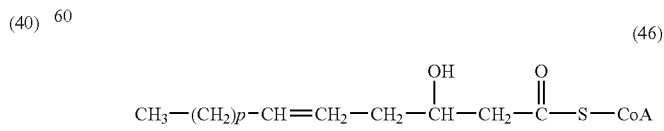
(46)

(wherein p represents an either integer of 3 or 5.)

(47)

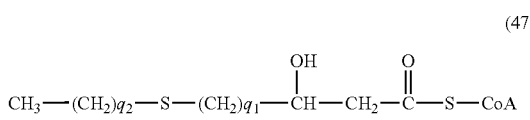

(wherein $q_1$ represents any of integers from 1 to 8, and $q_2$ represents any of integers from 0 to 8.)

(48)

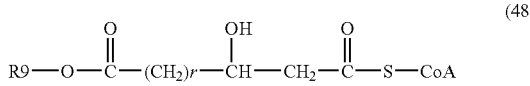

(wherein R9 is a hydrogen atom (H), Na atom or K atom, and r represents any of integers from 1 to 8.) In addition, when *Pseudomonas* sp. FA1 strain which is a bacterium for producing polyhydroxyalkanoate is used, trans-2,3-dehydroacyl-CoA, for example, those represented by the following chemical formulae (49) to (64) can be produced.

(49)

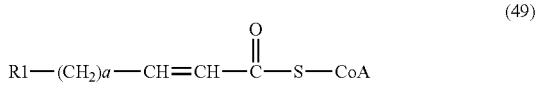

(wherein the trans-2,3-dehydroacyl-CoA is at least one selected from the group consisting those in which the combination of R1 and a is either one of the following:
(1) trans-2,3-dehydroacyl-CoA in which R1 is a hydrogen atom (H) and a is any of integers from 1 to 10,
(2) trans-2,3-dehydroacyl-CoA in which R1 is a halogen atom and a is any of integers from 1 to 10,
(3) trans-2,3-dehydroacyl-CoA in which R1 is

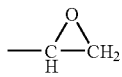

and a is any of integers from 1 to 8.)

(50)

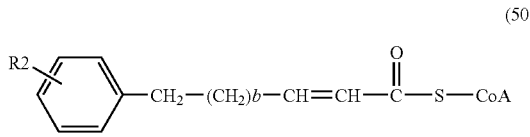

(wherein R2 represents a substituent group to the aromatic ring, and R2 represents either one selected from the group consisting of a hydrogen atom (H), a halogen atom, CN group, $NO_2$ group, COOR' (R': representing either one of H, Na and K) group, $CH_3$ group, $C_2H_5$ group, $C_3H_7$ group, $CH=CH_2$ group, $CF_3$ group, $C_2F_5$ group and $C_3F_7$ group, and b represents any of integers from 0 to 7).

(51)

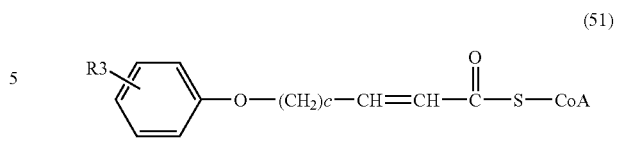

(wherein R3 represents a substituent group to the aromatic ring, and R3 represents either one selected from the group consisting of a hydrogen atom (H), a halogen atom, CN group, $NO_2$ group, $CH_3$ group, $C_2H_5$ group, $C_3H_7$ group, $SCH_3$ group, $CF_3$ group, $C_2F_5$ group and $C_3F_7$ group, and c represents any of integers from 0 to 7).

(52)

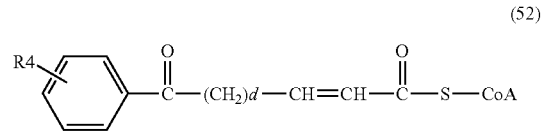

(wherein R4 represents a substituent group to the aromatic ring, and R4 represents either one selected from the group consisting of a hydrogen atom (H), a halogen atom, CN group, $NO_2$ group, $CH_3$ group, $C_2H_5$ group, $C_3H_7$ group, $CF_3$ group, $C_2F_5$ group and $C_3F_7$ group, and d represents any of integers from 0 to 7).

(53)

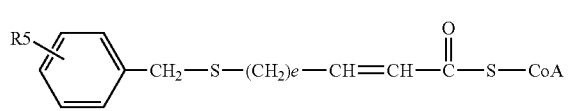

(wherein R5 represents a substituent group to the aromatic ring, and R5 represents either one selected from the group consisting of a hydrogen atom (H), a halogen atom, CN group, $NO_2$ group, COOR' (R': representing either one of H, Na, K, $CH_3$ and $C_2H_5$) group, $SO_2R''$ (R'': representing either one of OH, ONa, OK, a halogen atom, $OCH_3$ and $OC_2H_5$) group, $CH_3$ group, $C_2H_5$ group, $C_3H_7$ group, $CH(CH_3)_2$ group and $C(CH_3)_3$ group, and e represents any of integers from 1 to 8).

(54)

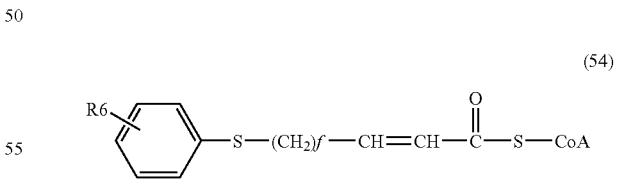

(wherein R6 represents a substituent group to the aromatic ring, and R6 represents either one selected from the group consisting of a hydrogen atom (H), a halogen atom, CN group, $NO_2$ group, COOR' (R': representing either one of H, Na, K, $CH_3$ and $C_2H_5$) group, $SO_2R''$ (R'': representing either one of OH, ONa, OK, a halogen atom, $OCH_3$ and $OC_2H_5$) group, $CH_3$ group, $C_2H_5$ group, $C_3H7$ group, $CH(CH_3)_2$ group and $C(CH_3)_3$ group, and f represents any of integers from 1 to 8).

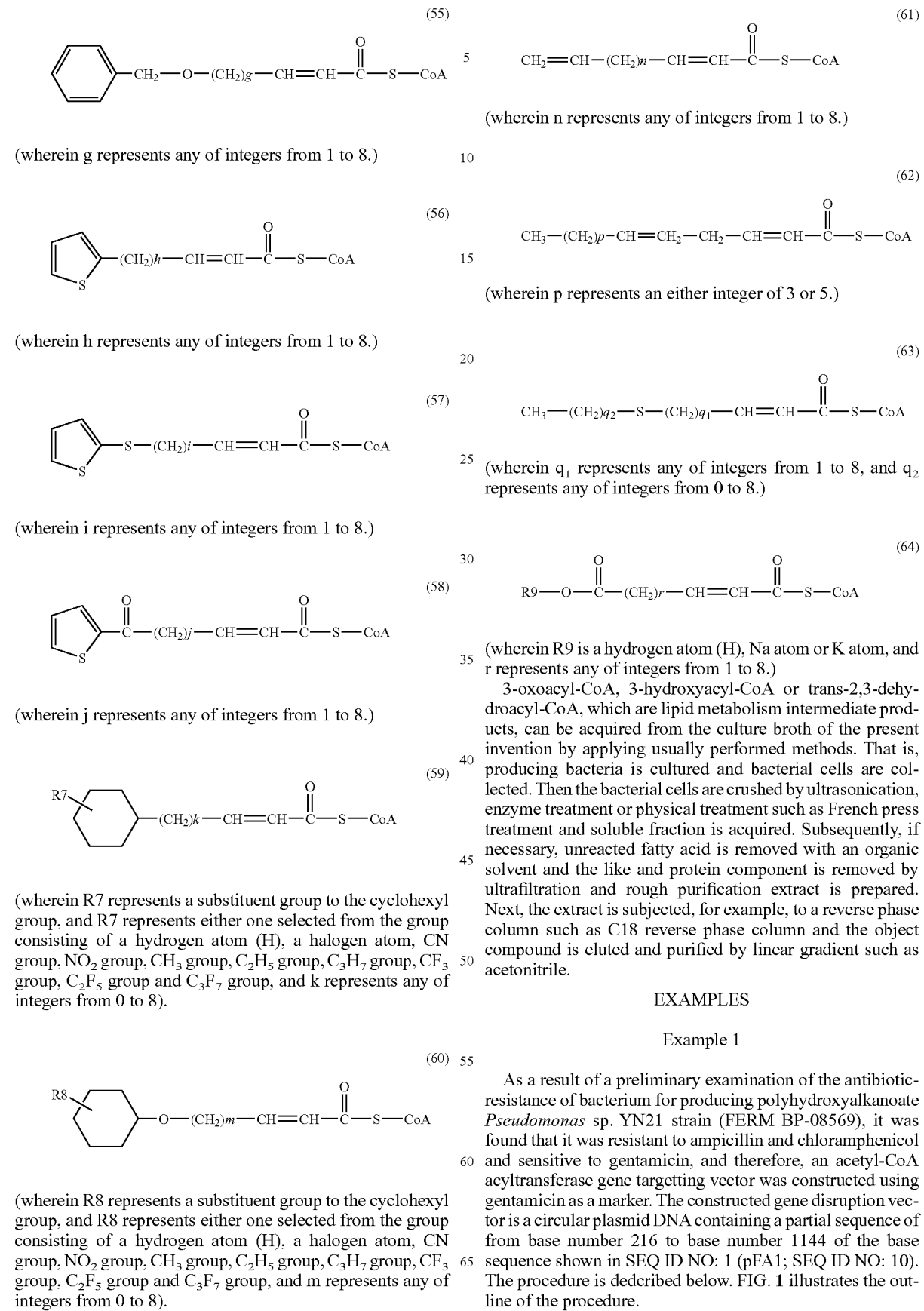

(wherein g represents any of integers from 1 to 8.)

(wherein h represents any of integers from 1 to 8.)

(wherein i represents any of integers from 1 to 8.)

(wherein j represents any of integers from 1 to 8.)

(wherein R7 represents a substituent group to the cyclohexyl group, and R7 represents either one selected from the group consisting of a hydrogen atom (H), a halogen atom, CN group, $NO_2$ group, $CH_3$ group, $C_2H_5$ group, $C_3H_7$ group, $CF_3$ group, $C_2F_5$ group and $C_3F_7$ group, and k represents any of integers from 0 to 8).

(wherein R8 represents a substituent group to the cyclohexyl group, and R8 represents either one selected from the group consisting of a hydrogen atom (H), a halogen atom, CN group, $NO_2$ group, $CH_3$ group, $C_2H_5$ group, $C_3H_7$ group, $CF_3$ group, $C_2F_5$ group and $C_3F_7$ group, and m represents any of integers from 0 to 8).

(wherein n represents any of integers from 1 to 8.)

(wherein p represents an either integer of 3 or 5.)

(wherein $q_1$ represents any of integers from 1 to 8, and $q_2$ represents any of integers from 0 to 8.)

(wherein R9 is a hydrogen atom (H), Na atom or K atom, and r represents any of integers from 1 to 8.)

3-oxoacyl-CoA, 3-hydroxyacyl-CoA or trans-2,3-dehydroacyl-CoA, which are lipid metabolism intermediate products, can be acquired from the culture broth of the present invention by applying usually performed methods. That is, producing bacteria is cultured and bacterial cells are collected. Then the bacterial cells are crushed by ultrasonication, enzyme treatment or physical treatment such as French press treatment and soluble fraction is acquired. Subsequently, if necessary, unreacted fatty acid is removed with an organic solvent and the like and protein component is removed by ultrafiltration and rough purification extract is prepared. Next, the extract is subjected, for example, to a reverse phase column such as C18 reverse phase column and the object compound is eluted and purified by linear gradient such as acetonitrile.

EXAMPLES

Example 1

As a result of a preliminary examination of the antibiotic-resistance of bacterium for producing polyhydroxyalkanoate Pseudomonas sp. YN21 strain (FERM BP-08569), it was found that it was resistant to ampicillin and chloramphenicol and sensitive to gentamicin, and therefore, an acetyl-CoA acyltransferase gene targetting vector was constructed using gentamicin as a marker. The constructed gene disruption vector is a circular plasmid DNA containing a partial sequence of from base number 216 to base number 1144 of the base sequence shown in SEQ ID NO: 1 (pFA1; SEQ ID NO: 10). The procedure is dedcribed below. FIG. 1 illustrates the outline of the procedure.

1) Preparation of Genomic DNA

*Pseudomonas* sp. YN21 strain was cultured in M9 culture medium containing 0.5% (w/v) of polypeptone at 30° C. for 24 hours. After harvesting the bacterial cells from the culture broth, genomic DNA of YN21 strain was prepared using Wizard, Genomic DNA Purification System (product of Promega Corp.).

2) Preparation of Insert DNA Fragment

PCR (Polymerase Chain Reaction) was performed using the genomic DNA of YN21 strain as a template and DNA of the base sequences represented by fadA-f1 (SEQ ID NO: 2) and fadA-r1 (SEQ ID NO: 3) as primers. The following reaction mixture was prepared.

TABLE 2

| | |
|---|---|
| Template (genomic DNA derived from YN21) | 250 ng |
| Primer fadA-f1 (SEQ ID NO: 2) | 250 pmol |
| Primer fadA-r1 (SEQ ID NO: 3) | 250 pmol |
| 10-fold amplification buffer | 5 µl |
| dNTP | 400 µM |
| Taq polymerase (LA-Taq, product of Takara Shuzo Co., Ltd.) | 2.5 U |
| Sterile distilled water | q.s. |
| Total | 50 µl |

PCR was performed by repeating 30 cycles of a series of treatment consisting of degeneration (at 98° C. for 20 seconds), annealing (at 65° C. for 20 seconds) and elongation (at 72° C. for 1 minute). The confirmation of PCR product was performed by agarose gel electrophoresis (gel concentration: 1 wt %). As a result, a fragment of about 480 base pairs was amplified. The PCR product of about 480 base pairs was excised from the agarose gel and the DNA fragment was collected using MinELute Gel Extraction Kit (product of Qiagen Co., Ltd.). PCR was performed using the genomic DNA of YN21 strain as a template and the collected DNA fragment of 480 base pairs and DNA of the base sequence represented by fadA-r2 (SEQ ID NO: 4) as primers. The following reaction mixture was prepared.

TABLE 3

| | |
|---|---|
| Template (genomic DNA derived from YN21) | 250 ng |
| PCR product of 480 base pairs | 250 pmol |
| Primer fadA-r2 (SEQ ID NO: 4) | 250 pmol |
| 10-fold amplification buffer | 5 µl |
| dNTP | 400 µM |
| Taq polymerase (LA-Taq, product of TaKaRa Shuzo Co., Ltd.) | 2.5 U |
| Sterile distilled water | q.s. |
| Total | 50 µl |

PCR was performed by repeating 30 cycles of a series of treatment consisting of degeneration (at 98° C. for 20 seconds), annealing (at 68° C. for 20 seconds) and elongation (at 72° C. for 1 minute). The confirmation of PCR product was performed by agarose gel electrophoresis (gel concentration: 1 wt %). As a result, a fragment of about 950 base pairs was amplified. The PCR product of about 950 base pairs was excised from the agarose gel and the DNA fragment was collected using MinELute Gel Extraction Kit (product of Qiagen, Inc.).

The base sequence of the PCR amplified product of about 950 base pairs was analyzed with Genetic Analyzer CEQ8000 (product of Beckman Coulter, Inc.) using DNA of base sequences represented by fadA-f1 (SEQ ID NO: 2) and fadA-r1 (SEQ ID NO: 3), DNA consisting of a base sequence complementary to the base sequence represented by SEQ ID NO: 3 or fadA-r2 (SEQ ID NO: 4) as primers. It was able to be confirmed that the amplified product was equivalent to a partial sequence from base number 200 to base number 1149 of DNA of SEQ ID NO: 1. As for the primers used for the above PCR, recognition site of restriction enzyme BamHI is contained in fadA-f1 (SEQ ID NO: 2), recognition site of restriction enzyme XbaI is contained in fadA-r1 (SEQ ID NO: 3) and recognition site of restriction enzyme SacI is contained in fadA-r2 (SEQ ID NO: 4), respectively beforehand. PCR amplified product of about 950 base pairs was digested with restriction enzymes BamHI and SacI.

The above-mentioned about 950 base pairs (1) forms a DNA-DNA hybrid with a DNA comprising a base sequence shown in SEQ ID NO: 1 by allowing hybridization in a high ion concentration (6×SSC (900 mM of sodium chloride, 90 mM of sodium citrate)) at a temperature condition of 65° C. and (2) maintains the DNA-DNA hybrid after washed in a low ion concentration (0.1×SSC (15 mM of sodium chloride, 1.5 mM of sodium citrate)) at a temperature condition of 65° C. for 30 minutes and it was confirmed that it was a DNA which hybridizes in a stringent condition. The detection of DNA-DNA hybrid was performed using AlkPhos Direct Labelling and Detection System (product of Amersham Biosciences Company).

3) Preparation of Vector DNA Fragment

PCR was performed using pEX100T (ATCC No. 87436) as a template and DNA of the base sequences represented by pEX-f1 (SEQ ID NO: 5) and pEX-r1 (SEQ ID NO: 6) as primers. The following reaction mixture was prepared.

TABLE 4

| | |
|---|---|
| Template (pEX100T) | 250 ng |
| Primer pEX-f1 (SEQ ID NO: 5) | 250 pmol |
| Primer pEX-r1 (SEQ ID NO: 6) | 250 pmol |
| 10-fold amplification buffer | 5 µl |
| dNTP | 400 µM |
| Taq polymerase (LA-Taq, product of TaKaRa Shuzo Co., Ltd.) | 2.5 U |
| Sterile distilled water | q.s. |
| Total | 50 µl |

PCR was performed by repeating 30 cycles of a series of treatment consisting of degeneration (at 98° C. for 20 seconds), annealing (at 65° C. for 20 seconds) and elongation (at 72° C. for 6 minutes). The confirmation of PCR product was performed by agarose gel electrophoresis (gel concentration: 1 wt %). As a result, a fragment of about 5.6 kb was amplified. Recognition site of restriction enzyme BamHI is contained in the used primer pEX-f1 (SEQ ID NO: 5) and recognition site of restriction enzyme SacI is contained in pEX-r1 (SEQ ID NO: 6), respectively beforehand. After the PCR product of 5.6 kb was digested with restriction enzymes BamHI and SacI, 5'-terminal end thereof was subjected to dephosphorylation treatment with Calf Intestine Alkaline Phosphatase (product of Takara Shuzo Co., Ltd.).

4) Ligation

The BamHI/SacI digestion product (insert) of about 950 base pairs prepared in the above 2) and the BamHI/SacI digestion product (vector) of about 5.6 kb prepared in the above 3) were ligated using DNA Ligation Kit Ver. 2 (product of Takara Shuzo Co., Ltd.). The composition of the ligation reaction mixture is shown below.

TABLE 5

| Insert DNA(0.3 pmol/µl) | 1 µl |
| --- | --- |
| Vector DNA(0.03 pmol/µl) | 4 µl |
| Enzyme Solution (attached to Kit) | 5 µl |
| Total | 10 µl |

Figure 3:
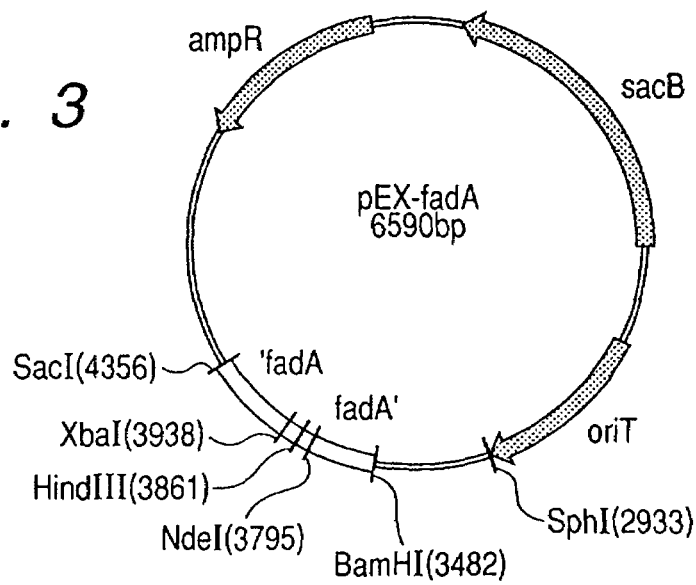
FIG. 3 is a restriction enzyme cleavage map of plasmid pEX-fadA constructed in Example 1.

After the ligation reaction mixture was held in an incubator at 16° C. for one hour, it was transformed into *Escherichia coli* JM109 competent cells. The colonies which could multiply on an LB agar plate containing 100 µg/ml of ampicillin were selected. As a result, plasmid pEX-fadA (SEQ ID NO: 7) was obtained. The restriction enzyme cleavage map of plasmid pEX-fadA was shown in FIG. 3.

5) Insertion of Gentamicin Cassette

After the plasmid pEk-fadA prepared in the above 4) was digested with restriction enzymes XbaI, 5'-terminal end thereof was subjected to dephosphorylation treatment with Calf Intestine Alkaline Phosphatase (product of Takara Shuzo Co., Ltd.). PCR was performed using pDONR207 (product of Invitrogen Co., Ltd.) as a template and DNA of the base sequences represented by gen-f1 (SEQ ID NO: 8) and gen-r1 (SEQ ID NO: 9) as primers. The following reaction mixture was prepared.

TABLE 6

| Template (pDONR207) | 250 ng |
| --- | --- |
| Primer gen-f1 (SEQ ID NO: 8) | 250 pmol |
| Primer gen-r1 (SEQ ID NO: 9) | 250 pmol |
| 10-fold amplification buffer | 5 µl |
| dNTP | 400 µM |
| Taq polymerase (LA-Taq, product of TaKaRa Shuzo Co., Ltd.) | 2.5 U |
| Sterile distilled water | q.s. |
| Total | 50 µl |

PCR was performed by repeating 30 cycles of a series of treatment consisting of degeneration (at 98° C. for 20 seconds), annealing (at 65° C. for 20 seconds) and elongation (at 72° C. for 1 minute). The confirmation of PCR product was performed by agarose gel electrophoresis (gel concentration: 1 wt %). As a result, a fragment of about 850 base pairs was amplified. Recognition site of restriction enzyme XbaI is contained in the used primers gen-f1 (SEQ ID NO: 8) and gen-r1 (SEQ ID NO: 9) beforehand and the PCR product of about 850 base pairs was digested with XbaI. The above XbaI digestion product (insert) of about 850 base pairs and XbaI digestion product (vector) of one pEX-fadA were ligated. The composition of the ligation reaction mixture is shown below.

TABLE 7

| Insert DNA(0.3 pmol/µl) | 1 µl |
| --- | --- |
| Vector DNA(0.03 pmol/µl) | 4 µl |
| Enzyme Solution(attached to Kit) | 5 µl |
| Total | 10 µl |

Figure 4:
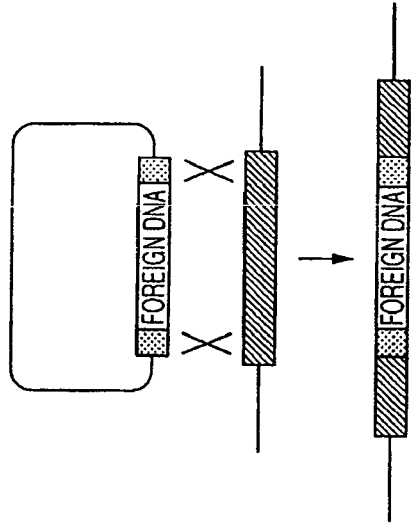
FIG. 4 is a restriction enzyme cleavage map of plasmid pFA1 (targeting vector for an acetyl-CoA acyltransferase gene) constructed in Example 1.

After the ligation reaction mixture was held in an incubator at 16° C. for one hour, it was transformed into Escherichia coli JM109 competent cells. The colonies which could multiply on an LB agar plate containing 15 µg/ml of gentamicin were selected. As a result, plasmid pFA1 (SEQ ID NO: 10) was obtained. The restriction enzyme cleavage map of plasmid pFA1 (targeting vector for an acetyl-CoA acyltransferase gene) was shown in FIG. 4.

Example 2

Acquisition of *Pseudomonas* sp. FA1 strain (FERM BP-08572), bacterium for producing polyhydroxyalkanoate in which the acetyl-CoA acyltransferase gene is disrupted Mobilizing strain *Escherichia coli* S17-1 (ATCC No. 47055) was transformed with the targeting vector for an acetyl-CoA acyltransferase gene (plasmid pFA1, SEQ ID NO: 10) constructed in Example 1 by electroporation method. Electroporation was conducted under the conditions of 2.5 kV, 25 µF and 2000 Ω, with a cell having a gap of 0.2 cm (Gene Pulsar cuvette 0.2 cm, product made in Bio-Rad Laboratories, Inc.) using a commercially available electroporation device (Gene Pulser, product made in Bio-Rad Laboratories, Inc.). The pFA1 transformant of S17-1 strain acquired as a colony which could multiply on an LB agar plate containing 15 µg/ml of gentamicin was subjected to shake culturing in 5 ml of LB liquid culture medium containing 100 µg/ml of ampicillin at 30° C. for 12 hours. Similarly, *Pseudomonas* sp. YN21 strain was subjected to shake culturing in 5 ml of LB liquid culture medium containing 100 µg/ml of ampicillin at 30° C. for 12 hours.

150 µl of the culture broth of the pFA1 transformant of *E. coli* S17-1 strain was inoculated to 150 ml of LB liquid culture medium containing 100 µg/ml of ampicillin and shake cultured at 30° C. while monitoring absorbance at 600 nm at any time (sterilized LB liquid culture medium was used as control). In addition, 150 µl of the culture broth of YN21 strain was also inoculated to 150 ml of LB liquid culture medium containing 100 µg/ml of ampicillin and shake cultured at 30° C. while monitoring absorbance at 600 nm at any time (sterilized LB liquid culture medium was used as control). 4.5 ml of the culture broth of the pFA1 transformant of *E. coli* S17-1 strains (absorbance at 600 nm was 0.35) and 0.5 ml of the culture broth of YN21 strain (absorbance at 600 nm was 0.39) were mixed and filtered with a nitrocellulose filter (pore size: 0.45 µm, diameter: 25 mm, white surfactant free HATF manufactured by Millipore, Corp.) and cells were collected.

The nitrocellulose filter was placed on an LB agar plate with the surface on which the cells were collected in the upward direction, and the agar plate was covered with a lid so that the agar plate might not be dried, and maintained at a constant temperature of 30° C. for 90 minutes. The bacterial cells on the filter were suspended by pipetting in 1 ml of LB liquid culture medium containing 100 µg/ml of ampicillin, and a suitable amount of the suspension was seeded on an LB agar plate containing 15 µg/ml of gentamicin and 10 µg/ml chloramphenicol. Colonies which appeared after culturing at 30° C. for two days were streaked on an LB agar plate containing 15 µg/ml gentamicin, 10 µg/ml chloramphenicol and 5% (w/v) of sucrose and cultured at 30° C. for two days. Some of the colonies which grew on the LB agar plate containing 15 µg/ml gentamicin, 10 µg/ml chloramphenicol and 5% (w/v) of sucrose were cultured in M9 culture medium containing 15 µg/ml gentamicin, 10 µg/ml chloramphenicol and 0.5 wt % of polypeptone at 30° C. for 24 hours. After the bacterial cells were collected from the culture broth, Genomic DNA was prepared using Wizard Genomic DNA Purification System (product of Promega Corp.).

PCR was performed using as templates the prepared genomic DNA and one prepared in genomic DNA (above 1) of YN21 strain as control and DNA of the base sequences represented by fadA-f1 (SEQ ID NO: 2) and fadA-r2 (SEQ ID NO: 4) as primers. The following reaction mixture was prepared.

TABLE 8

| | |
|---|---|
| Template (genomic DNA) | 250 ng |
| Primer fadA-f1 (SEQ ID NO: 2) | 250 pmol |
| Primer fadA-r2 (SEQ ID NO: 4) | 250 pmol |
| 10-fold amplification buffer | 5 μl |
| dNTP | 400 μM |
| Taq polymerase (LA-Taq, product of TaKaRa Shuzo Co., Ltd.) | 2.5 U |
| Sterile distilled water | q.s. |
| Total | 50 μl |

PCR was performed by repeating 30 cycles of a series of treatment consisting of degeneration (at 98° C. for 20 seconds), annealing (at 64° C. for 20 seconds) and elongation (at 72° C. for 2 minutes). The confirmation of PCR product was performed by agarose gel electrophoresis (gel concentration: 1 wt %). As a result, a fragment of about 1.5 kb pairs was amplified when the genomic DNA was used as a template and a fragment of about 740 base pairs was amplified when the genomic DNA prepared from YN21 strain as control was used as a template, respectively. This means that DNA containing a gentamicin resistant gene was inserted in the middle of the acetyl-CoA acyltransferase gene in the newly acquired colony, and the length of DNA fragment amplified by PCR increased thereby, and that the acetyl-CoA acyltransferase gene was disrupted.

Example 3

Production of PHA Using FA1 Strain in which the Acetyl-CoA Acyltransferase Gene is Disrupted FA1 strain or YN21 strain as control were inoculated to 200 mL of M9 culture medium containing 0.2% (w/v) of polypeptone, 0.2% (w/v) of glucose and 0.1% (v/v) of nonanoic acid, and shake cultured at 30° C. with 125 strokes/min. The bacterial cells were collected by centrifugal separation in 90 hours and freeze-dried after washed with a cold methanol once. This freeze-dried pellet was suspended in 100 mL of chloroform and agitated at 60° C. for 20 hours to extract PHA. The extract was filtered with a membrane filter having a pore size of 0.45 μm, then concentrated with rotary evaporator and the concentrate was allowed to deposit again in cold methanol and only the precipitation was collected and vacuum dried to obtain PHA. The molecular weight of the obtained PHA was measured by gel permeation chromatography (GPC; Tosoh HLC-8020, column: Polymer laboratory PLgel MIXED-C (5 μm), solvent: chloroform, polystyrene conversion). The obtained PHA was subjected to methanolysis according to a conventional method and then analyzed by gas chromatography mass spectrometry device (GC-MS, Shimadzu QP-5050, EI method) and a methyl ester of PHA monomer unit was identified. The results were shown in Table 9.

TABLE 9

| Strain | FA1 | YN21(Control) |
|---|---|---|
| Dry weight of cells | 0.49[g/L] | 1.15[g/L] |
| Dry weight of polymer | 0.12[g/L] | 0.48[g/L] |
| Dry weight of polymer/Dry weight of cells | 25% | 42% |
| Number average molecular weight | 77,000 | 109,000 |
| Weight average molecular weight | 198,000 | 209,000 |

TABLE 9-continued

| Strain | FA1 | YN21(Control) |
|---|---|---|
| Composition of monomer unit (area ratio) | | |
| 3-Hydroxybutyric acid | 1.3% | 1.5% |
| 3-Hydroxyvaleric acid | 0% | 0.7% |
| 3-Hydroxyhexanoic acid | 0% | 0% |
| 3-Hydroxyheptanoic acid | 3.1% | 23.6% |
| 3-Hydroxyoctanoic acid | 0% | 0% |
| 3-Hydroxynonanoic acid | 95.6% | 74.2% |
| 3-Hydroxydecanoic acid | 0% | 0% |

As is apparent from the results in Table 9, PHA produced by FA1 strain scarcely contains those units shorteded in the chain length even when an "usual monomer substrate" was used due to the disruption of the acetyl-CoA acyltransferase gene and it was found to be useful for producing homopolymer of such polyhydroxyalkanoates.

Example 4

Production of PHA Using FA1 Strain in which the Acetyl-CoA Acyltransferase Gene is Disrupted FA1 strain or YN21 strain as control were inoculated to 200 mL of M9 culture medium containing 0.5% (w/v) of polypeptone, 0.2% (w/v) of yeast extract and 0.1% (v/v) of 7-phenylheptanoic acid, and shake cultured at 30° C. with 125 strokes/min. The bacterial cells were collected by centrifugal separation in 90 hours and freeze-dried after washed with a cold methanol once. This freeze-dried pellet was suspended in 100 mL of chloroform and agitated at 60° C. for 20 hours to extract PHA. The extract was filtered with a membrane filter having a pore size of 0.45 μm, then concentrated with rotary evaporator and the concentrate was allowed to deposit again in cold methanol and only the precipitation was collected and vacuum dried to obtain PHA. The obtained PHA was subjected to methanolysis according to a conventional method and then analyzed by gas chromatography mass spectrometry device (GC-MS, Shimadzu QP-5050, EI method) and a methyl ester of PHA monomer unit was identified. The results were shown in Table 10.

TABLE 10

| Strain | FA1 | YN21(Control) |
|---|---|---|
| Dry weight of cells | 1.42[g/L] | 1.96[g/L] |
| Dry weight of polymer | 0.54[g/L] | 0.87[g/L] |
| Dry weight of polymer/Dry weight of cells | 38% | 45% |
| Composition of monomer unit (area ratio) | | |
| 3-Hydroxybutyric acid | 0% | 1.2% |
| 3-Hydroxy-5-phenylvaleric acid | 11.0% | 81.5% |
| 3-Hydroxy-7-phenylheptanoic acid | 89.0% | 17.3% |

As is apparent from the results in Table 10, PHA produced by FA1 strain scarcely contains those units shorteded in the chain length even when an "unusual monomer substrate" was used due to the disruption of the acetyl-CoA acyltransferase gene and it was found to be useful for producing PHA of the composition utterly different from the monomer unit composition of the conventional polyhydroxyalkanoates.

Example 5

Production of Fatty Acid Metabolic Intermediates

FA1 strain or YN21 strain as control were inoculated to 200 mL of M9 culture medium containing 0.2% (w/v) of polypeptone, 0.2% (w/v) of glucose and 0.1% (v/v) of octanoic acid, and shake cultured at 30° C. with 125 strokes/min. The bacterial cells were collected by centrifugal separation in 90 hours and suspended in PBS buffer solution. The cell suspension was subjected to French press treatment to crush the cells and then centrifuged and the supernatant was prepared as a soluble fraction. Enzymes and the like were separated and removed from the soluble fraction using Amicon Centriprep membrane (molecular mass cutoff of 10,000). Next, 3-oxooctanoyl-CoA, 3-hydroxyoctanoyl-CoA and trans-2,3-dehydrooctanoyl-CoA were eluted with methanol using $C_{18}$ cartridge ($C_{18}$ silica Bondelut 500 mg, 3 ml, Valian Benelux), and roughly purified. After methanol was evaporated in a nitrogen stream, the residue was dissolved in 50 mM potassium phosphate, pH 5.5 (Buffer A) and place on Econosphere C18 column (150×4.6 mm, 80 Å, 5 µm, Alltech)/Waters gradient HPLC system. 3-oxooctanoyl-CoA, 3-hydroxyoctanoyl-CoA and trans-2,3-dehydrooctanoyl-CoA were eluted by linear gradient acetonitrile in Buffer A and purified. 3-oxooctanoyl-CoA, 3-hydroxyoctanoyl-CoA and trans-2,3-dehydrooctanoyl-CoA were detected and fractioned by determining the amount of adenine in the CoA derivatives measuring the absorbance ($\epsilon$, 16,400 $M^{-1}$ $cm^{-1}$) at 259 nm. 3-oxooctanoyl-CoA, 3-hydroxyoctanoyl-CoA and trans-2,3-dehydrooctanoyl-CoA were analyzed directly or based on released acyl group after causing selective breakage of thioester bond by adding 25 mM hydroxy amine using LC-MS (LCQ Advantage, Thermo Finnigan) and each of them was identified. They were also quntified by detecting CoA released by selective breakage of thioester bond by adding 25 mM hydroxy amine using DTNB ($\epsilon$, 14,100 $M^{-1}$ $cm^{-1}$). As a result, it proved that FA1 strain is superior to YN21 strain in productivity for all of 3-oxooctanoyl-CoA, 3-hydroxyoctanoyl-CoA and trans-2,3-dehydrooctanoyl-CoA.

Example 6

Production of PHA Using FA1 Strain in which the Acetyl-CoA Acyltransferase Gene is Disrupted Each of the culture media in which alkanoic acids shown in the below Table 11 were individually added to 50 mL of M9 culture medium containing polypeptone and 0.5% (w/v) of polypeptone and 0.5% (w/v) of glucose was prepared.

TABLE 11

| Medium identification number | Alkanoic acid added to medium |
|---|---|
| 6-1 | 6 mM 7,8-epoxyoctanoic acid |
| 6-2 | 6 mM 4-phenoxy-n-butyric acid |
| 6-3 | 6 mM 5-(4-fluorobenzoyl)valeric acid |
| 6-4 | 6 mM 5-{[(4-fluorophenyl)methyl]sulfanyl}valeric acid |
| 6-5 | 6 mM 4-(phenylsulfanyl)butyric acid |
| 6-6 | 6 mM 5-phenylmethyloxyvaleric acid |
| 6-7 | 6 mM 5-(2-thienyl)valeric acid |
| 6-8 | 6 mM 5-(2-thienylsulfanyl)valeric acid |
| 6-9 | 6 mM 5-(2-thienoyl)valeric acid |
| 6-10 | 6 mM 4-cyclohexylbutyric acid |
| 6-11 | 6 mM 4-cyclohexyloxybutyric acid |
| 6-12 | 6 mM 10-undecenoic acid |
| 6-13 | 6 mM dodec-5-enoic acid |
| 6-14 | 6 mM 5-(methylthio)valeric acid |

FA1 strain or YN21 strain as control were inoculated, and shake cultured at 30° C. with 125 strokes/min for 96 hours. The bacterial cells were collected by centrifugal separation and freeze-dried after washed with a cold methanol once. This freeze-dried pellet was suspended in 100 mL of chloroform and agitated at 60° C. for 20 hours to extract PHA. The extract was filtered with a membrane filter having a pore size of 0.45 µm, then concentrated with rotary evaporator and the concentrate was allowed to deposit again in cold methanol and only the precipitation was collected and vacuum dried to obtain PHA.

Monomer unit ratio of the obtained PHA was determined by $^1$H-NMR (FT-NMR: BrukerDPX400, Resonance frequency: 400 MHz, Measured nuclide: 1H, Used solvent: $CDCl_3$, reference: capillary contained TMS/$CDCl_3$, Measurement temperature: room temperature) The results of polymer dry weight (PDW) and monomer unit ratio were shown in Table 12.

TABLE 12

| Medium identification number | FA 1 | | YN 21 | |
|---|---|---|---|---|
| | PDW (g/L) | Monomer unit ratio (mol %) | PDW (g/L) | Monomer unit ratio (mol %) |
| 6-1 | 0.92 | 3-hydroxy-7,8-epoxyoctanoic acid 94% | 1.08 | 3-hydroxy-7,8-epoxyoctanoic acid 72% |
| 6-2 | 0.89 | 3-hydroxy-4-phenoxy-n-butyric acid 84% | 1.05 | 3-hydroxy-4-phenoxy-n-butyric acid 61% |
| 6-3 | 0.74 | 3-hydroxy-5-(4-fluorobenzoyl)valeric acid 85% | 0.87 | 3-hydroxy-5-(4-fluorobenzoyl)valeric acid 55% |
| 6-4 | 0.76 | 3-hydroxy-5-{[(4-fluorophenyl)methyl]sulfanyl}valeric acid 84% | 0.89 | 3-hydroxy-5-{[(4-fluorophenyl)methyl]sulfanyl}valeric acid 64% |
| 6-5 | 0.81 | 3-hydroxy-4-(phenylsulfanyl)butyric acid 85% | 0.95 | 3-hydroxy-4-(phenylsulfanyl)butyric acid 62% |
| 6-6 | 0.75 | 3-hydroxy-5-phenylmethyloxyvaleric acid 84% | 0.88 | 3-hydroxy-5-phenylmethyloxyvaleric acid 62% |
| 6-7 | 0.74 | 3-hydroxy-5-(2-thienyl)valeric acid 85% | 0.87 | 3-hydroxy-5-(2-thienyl)valeric acid 62% |

TABLE 12-continued

| Medium | FA 1 | | YN 21 | |
|---|---|---|---|---|
| identification number | PDW (g/L) | Monomer unit ratio (mol %) | PDW (g/L) | Monomer unit ratio (mol %) |
| 6-8 | 0.84 | 3-hydroxy-5-(2-thienylsulfanyl)valeric acid 84% | 0.99 | 3-hydroxy-5-(2-thienylsulfanyl)valeric acid 62% |
| 6-9 | 0.75 | 3-hydroxy-5-(2-thienoyl)valeric acid 94% | 0.88 | 3-hydroxy-5-(2-thienoyl)valeric acid 52% |
| 6-10 | 0.83 | 3-hydroxy-4-cyclohexylbutyric acid 84% | 0.98 | 3-hydroxy-4-cyclohexylbutyric acid 62% |
| 6-11 | 0.92 | 3-hydroxy-4-cyclohexyloxybutyric acid 84% | 1.08 | 3-hydroxy-4-cyclohexyloxybutyric acid 54% |
| 6-12 | 0.89 | 3-hydroxy-10-undecenoic acid 85% | 1.05 | 3-hydroxy-10-undecenoic acid 64% |
| 6-13 | 0.70 | 3-hydroxy-dodec-5-enoic acid 94% | 0.82 | 3-hydroxy-dodec-5-enoic acid 53% |
| 6-14 | 0.77 | 3-hydroxy-5-(methylthio)valeric acid 85% | 0.91 | 3-hydroxy-5-(methylthio)valeric acid 52% |

As is apparent from the results in Table 12, PHA produced by FA1 strain scarcely contains those units shortened in the chain length even when an "unusual monomer substrate" was used due to the disruption of the acetyl-CoA acyltransferase gene and it was found to be useful for producing PHA of the composition utterly different from the monomer unit composition of the conventional polyhydroxyalkanoates.

Example 7

Disruption of the Acetyl-CoA Acyltransferase Gene Using a Mutant Targeting Vector For plasmid pEX-fadA (SEQ ID NO: 7) prepared in Example 1, the base sequence GGC from the 3685th to 3687th was substituted to GCC, the base sequence TAC from the 3850th to the 3852nd was substituted to CAT and the base sequence ACC from the 4042nd to the 4044th to GTC respectively. The substitution of each base sequence was performed with Quick Change Multi Site-Directed Mutagenesis Kit (Stratagene) using the plasmid as a template. The BamHI and SacI digested product (about 870 bp) of the mutant plasmid (1) forms a DNA-DNA hybrid with a DNA comprising a base sequence shown in SEQ ID NO: 1 by allowing hybridization in a high ion concentration (6×SSC (900 mM of sodium chloride, 90 mM of sodium citrate)) at a temperature condition of 65° C. and (2) and maintains the DNA-DNA hybrid after washed in a low ion concentration (0.1×SSC (15 mM of sodium chloride, 1.5 mM of sodium citrate)) at a temperature condition of 65° C. for 30 minutes and it was confirmed that it was a DNA which hybridizes in a stringent condition. The detection of DNA-DNA hybrid was performed using Alk-Phos Direct Labelling and Detection System (product of Amersham Biosciences Company).

A targeting vector for an acetyl-CoA acyltransferase gene mutated by introducing a gentamicin cassette into a XbaI site of the plasmid following the method dscribed in Example 1.

Polyhydroxyalkanoate producing bacteria in which the acetyl-CoA acyltransferase gene was disrupted was able to be acquired by the method dscribed in Example 2 using the prepared gene targeting vector.

Example 8

Acquisition of YN21 Strain

M9 culture medium containing 0.5% of polypeptone, 0.1% of phenylvaleric acid, 0.3% of mineral solution and 1.2% of powder agar was autoclave sterilized and after cooled to 50° C., DMSO solution containing 0.05% of Nile red was added in a ratio of 0.1% and 15 ml aliquot was put into sterilized petri dishes and agar media were prepared by solidifying the agar.

The composition of M9 culture medium and mineral solution are shown below.

<M9 Culture Medium>

$Na_2HPO_4$: 6.2 g, $KH_2PO_4$: 3.0 g, NaCl: 0.5 g, $NH_4Cl$: 1.0 g (per 1 liter of culture medium, PH7)

<Mineral Solution>

Nitrilotriacetic acid: 1.5 g, $MgSO_4$: 3.0 g, $MnSO_4$: 0.5 g, NaCl: 1.0 g, $FeSO_4$: 0.1 g, $CaCl_2$: 0.1 g, $CoCl_2$: 0.1 g, $ZnSO_4$: 0.1 g, $CuSO_4$: 0.1 g, $AlK(SO_4)_2$: 0.1 g, $H_3BO_3$: 0.1 g, $Na_2MoO_4$: 0.1 g, $NiCl_2$: 0.1 g (in 1 liter PH7.)

Next, 5 g of soil sample taken from the outdoors was added to 10 ml of sterile distilled water and agitated for one minute. 0.5 ml of this soil suspension was added to 4.5 ml of sterile water and agitated to prepare 10-fold dilute solution. Similar operation was repeated and 100-fold dilute solution, 1,000-fold dilute solution and 10,000-fold dilute solution were prepared. Each 0.1 ml of the 10-fold to 10,000-fold dilute solutions was put in the agar media prepared above and uniformly spread on the agar surface. These were transferred to an incubator and cultured at 30° C. for five days. After culturing, strains of different morphology were separated from among the red colonies which seemed to synthesized PHA. More than a dozen wild type strains were acquired in this way. These wild type strains were inoculated from the colonies of the preserved agar media to 50 ml of M9 culture medium (pH 7.0) containing 0.5% of polypeptone, 0.5% of glucose, 0.1% of phenylvaleric acid, 0.3% of mineral solution and shake cultured in 500 ml volume Sakaguchi flask at 30° C., with 125 strokes/min. Culturing was also performed similarly in culture media mention above but with pH respectively adjusted to 5.0, PH8.5. The bacterial cells were collected by centrifugal separation in 72 hours and freeze-dried after washed with a cold methanol once. This freeze-dried pellet was suspended in 10 mL of ethyl acetate and agitated at 35° C. for 15 hours to extract PHA. The extract was filtered with a membrane filter having a pore size of 0.45 μm, then concentrated with rotary evaporator. The concentrate was added to cold methanol and allowed to deposit again and only the precipitation was collected and vacuum dried. The obtained PHA was weighed and the polymer drying weight (PDW) was determined. Monomer unit ratio of the obtained PHA was determined by $^{1}$H-NMR (FT-NMR: BrukerDPX400, Resonance frequency: 400 MHz, Measured nuclide: 1H, Used solvent: CDCl3, reference: capillary contained TMS/CDCl3, Measurement temperature: room temperature). YN21 strain having PHA productivity was acquired by comparing monomer drying weight (PDW) and monomer unit ratio thus obtained.

This application claims priority from Japanese Patent Application No. 2005-023964 filed Jan. 31, 2005, which is hereby incorporated by reference herein.

What is claimed is:

1. An isolated *Pseudomonas* sp. FA1 strain (FERM BP-08572) which is an isogenic strain of the polyhydroxyalkanoate-producing bacterium *Pseudomonas* sp. YN21 strain (FERM BP-08569) in which a gene encoding acetyl-CoA acyltransferase is disrupted.

* * * * *